United States Patent [19]
Bochner

[11] Patent Number: 6,136,554
[45] Date of Patent: Oct. 24, 2000

[54] MICROBIOLOGICAL MEDIA FOR ISOLATION AND INDENTIFICATION OF ENTERIC PATHOGENS SUCH AS E. COLI AND SALMONELLA

[75] Inventor: Barry Bochner, Alameda, Calif.

[73] Assignee: Biolog, Inc., Calif.

[21] Appl. No.: 08/819,452

[22] Filed: Mar. 17, 1997

Related U.S. Application Data

[63] Continuation of application No. 08/484,960, Jun. 7, 1995.

[51] Int. Cl.[7] .............................. C12Q 1/04; C12N 1/00
[52] U.S. Cl. ......................... 435/34; 435/243; 435/244; 435/245; 435/253.6
[58] Field of Search ............................... 435/243, 253.6, 435/34, 244, 245

[56] References Cited

U.S. PATENT DOCUMENTS

| | | | |
|---|---|---|---|
| 3,870,601 | 3/1975 | Warren | 435/243 |
| 3,957,584 | 5/1976 | Kronish | 435/243 |
| 4,070,247 | 1/1978 | Burt | 195/100 |
| 4,235,964 | 11/1980 | Bochner | 435/34 |
| 4,241,186 | 12/1980 | Roth | 435/243 |
| 4,282,317 | 8/1981 | Roth | 435/34 |
| 4,326,052 | 4/1982 | Kang et al. | 536/1 |
| 4,326,053 | 4/1982 | Kang et al. | 536/1 |
| 5,093,832 | 3/1992 | Rambach | 435/34 |
| 5,128,457 | 7/1992 | Albarella et al. | . |
| 5,149,656 | 9/1992 | Bilton | 435/288 |
| 5,187,265 | 2/1993 | Albarella et al. | . |
| 5,194,374 | 3/1993 | Rambach | 435/34 |
| 5,208,150 | 5/1993 | Tate et al. | 435/38 |
| 5,210,022 | 5/1993 | Roth et al. | 435/34 |
| 5,212,067 | 5/1993 | Mallinson et al. | . |

FOREIGN PATENT DOCUMENTS

| | | | |
|---|---|---|---|
| 79400638 | 3/1981 | European Pat. Off. | 1/4 |
| 91105584 | 10/1991 | European Pat. Off. | . |
| WO 82/02563 | 8/1982 | WIPO | 1/4 |
| WO 94/08043 | 4/1994 | WIPO | 1/10 |

OTHER PUBLICATIONS

Ho, M–S, et al., "Rotavirus as a cause of diarrheal morbidity and mortality in the United States," J. Infect. Dis., 158:1112–1116 (1988).
Snyder, J.D. & Merson, M.H., "The magnitude of the global problem of acute diarrheal disease: a review of active surveillance data," Bull. World Health Organ., 60:605–613 (1982).
Hale, T.L., "Genetic basis of virulence in Shigella species," Microbiol. Rev., 55:206–224 (1991).
Singh and McFeters, "Detection methods for waterborne pathogens," in *Environmental Microbiology*, R. Mitchell (ed.), Wiley–Liss, New York, pp.125–156 (1992).
Makintubee, S., "Shigellosis outbreak associated with swimming," Am. J. Public Health, 77:166–168 (1987).
Sorvillo, F.J., et al., "Shigellosis associated with recreational water contact in Los Angeles County," Am. J. Trop. Med. Hyg., 38: 613–617 (1988).
Hazen, T.C. & Toranzos, G.A., "Tropical Source Water," p. 33–53 in *Drinking Water Microbiology*, G.A. McFeters (ed.), Springer–Verlag, New York, pp. 33–53 (1990).
Byrd, J.J., et al., "Viable but nonculturable bacteria in drinking water," Appl. Environ. Microbiol., 57:875–878 (1991).
Desmonts, C., et al., "Fluorescent–antibody method useful for detecting viable but nonculturable Salmonella spp. in chlorinated wastewater," Appl. Environ. Microbiol., 56:1448–1452 (1990).
Byrd, J.J. & Colwell, R.R., "Maintenance of plasmids pBR322 and pUC8 in nonculturable *Escherichia coli* in the marine environment," Appl. Environ. Microbiol., 56:2104–2107 (1990).
Morris, J.G., "Watching the birds (and the beef): New approaches to meat and poultry inspection," ASM News, 61:56–57 (1995).
USDA, "Pathogen reduction. Hazard analysis and critical control point (HACCP) systems," Federal Register Part II 60(023):6774 (Friday, Feb. 3, 1995).
Black, J.D., *Microbiology Principles and Applications*, 2d edition, Prentice Hall, New Jersey, p. 751 (1993).
Fox, J.L. "USDA's food–safety push boosts assay makers," Bio/Technol., 13:114–115, (1995).
Baron, E.J. & Finegold, S., *Diagnostic Microbiology*, 8th ed., C.V. Mosby, St. Louis, p. 253 (1990).
Farmer, J.J. & Kelly, M.T., "Enterobacteriaceae," in *Manual of Clinical Microbiology*, Balows et al. (eds.), American Society for Microbiology, p. 366 (1991).
Karmali, M.A., "Infection by verocytotoxin–producing *Escherichia coli*," Clin. Microbiol. Rev., 2:15–38 (1989).
Riley, L.W., et al., "Hemorrhagic colitis associated with a rare *Escherichia coli* serotype," New Eng. J. Med., 308:681–685 (1983).
Krishman, C., et al., "Laboratory investigation of outbreak of hemorrhagic colitis caused by *Escherichia coli* 0157:H7," J. Clin. Microbiol., 25:1043–1047 (1987).
Padhye, N.V. & Doyle, M.P., "*Escherichia coli* 0157:H7: Epidemiology, pathogenesis and methods for detection in food," J. Food Prot., 55:555–565 (1992).
Pierard, D., et al., "Results of screening for verocytotoxin–producing *Escherichia coli* in faeces in Belgium," Eur. J. Clin. Microbiol. Infect. Dis., 9:198–201 (1990).
Griffin, P.M. & Tauxe, R.V., "The epidemiology of infections caused by *Escherichia coli* 0157:H7, other enterohemorrhagic *E. coli*, and the associated hemolytic uremic syndrome," Epidemiol. Rev., 13: 60–98 (1991).

(List continued on next page.)

*Primary Examiner*—Irene Marx
*Attorney, Agent, or Firm*—Medlen & Carroll, LLP

[57] ABSTRACT

The present invention is directed to methods and media for the growth, enrichment, isolation, and presumptive identification of enteric pathogens such as *E. coli* 0157:H7 and Salmonella. In particular, the organisms commonly associated with gastrointestinal infections of humans and other animals are distinguished based on their growth, colonial morphology and color. The present invention is also directed to methods and media for the growth, enrichment, isolation and presumptive identification of enteric pathogens such as *E. coli* 0157:H7 and Salmonella isolated from food, water, dairy, and environmental samples.

21 Claims, No Drawings

OTHER PUBLICATIONS

Tarr, P.I., "Review of 1993 *Escherichia coli* O157:H7 outbreak: Western United States," Dairy Food & Environ. Sanitation 14:372–373 (1994).

Recer, P., "Experts call for irradiation of meat to protect against food–borne bacteria," Associated Press, Jul. 12, 1994.

Bielszewska et al., "Verotoxigenic (enterohaemorrhagic) *Escherichia coli* in infants and toddlers in Czechoslovakia," Infection 18:352–356 (1990).

Caprioli, A., et al., "Hemolytic–uremic syndrome and Vero cytotoxin producing *Escherichia coli* infection in Italy," J. Infect. Dis., 166:154–158 (1992).

Caprioli, A., et al., "Community–wide outbreak of hemolytic–uremic syndrome associated with non–O157 verocytotoxin–producing *Escherichia coli*," J. Infect Dis., 169:208–211 (1994).

Cimolai, N., "Low Frequency of high level Shiga–like toxin productions in enteropathogenic *Escherichia coli* serogroups," Eur. J. Pediatr., 151:147 (1992).

Wells, J.G., et al., "Laboratory investigation of hemorrhagic colitis outbreaks associated with a rare *Escherichia coli* serotype," J. Clin. Microbiol., 18:512–520 (1983).

Voelker, R., "Panel calls *E. coli* screening inadequate," *Escherichia coli* 0157:H7—Panel sponsored by the American Gastroenterological Association Foundation in Jul. 1994, Medical News & Perspectives, J. Amer. Med. Assoc., 272:501 (1994).

Neill, M.A.,"*E. coli* O157:H7 time capsule: What do we know and when did we know it?," Dairy Food & Environ. Sanitation 14:374–377 (1994).

Levine, M.M., et al., "Antibodies to Shiga holotoxin and to two synthetic peptides of the B subunit in sera of patients with *Shigella dysenteriae* 1 dysentery," J. Clin. Microbiol., 30:1636–1641 (1992).

Molenda, J.R., et al., "*Escherichia coli* (including 0157:H7): An environmental health perspective," Dairy Food & Environ. Sanitation 14:742–747 (1994).

Dorn, C.R., et al., "Properties of Vero cytotoxin producing *Escherichia coli* of human and animal origin belonging to serotypes other than 0157:H7," Epidemiol. Infect., 103:83–95 (1989).

Centers for Disease Control, "Public Health Threats," Science 267:1427 (1995).

Harris, A.A., et al., "Results of a screening method used in a 12 month stool survey for *Escherichia coli* 0157:H7," J. Infect. Dis., 152:775–777 (1985).

Pai, C.H., et al., "Sporadic cases of hemorrhagic colitis associated with *Escherichia coli* 0157:H7," Ann. Intern. Med., 101:738–742 (1984).

Pudden, D., et al.,"Hemorrhagic colitis in a nursing home," Ontario Can. Dis. Weekly Rpt., 11:169–170 (1985).

Kwaan, H.C., "Clinicopathological features of thrombotic thrombocytopenic purpura," Semin. Hematol., 24:71–81 (1987).

Machin, S.J., "Clinical annotation: Thrombotic thrombocytopenic purpura," Br. J. Hematol., 56:191–197 (1984).

Amorosi, E.L. & Ultmann, J.E., "Thrombotic thrombocytopenic purpura: Report of 16 cases and review of the literature," Med., 45:139–159 (1966).

Grandsen, W.R., et al., "Hemorrhagic cystitis and balanitis associated with verotoxin–producing *Escherichia coli* 0157:H7," Lancet ii:150 (1985).

Rowe, P.C., et al., "Hemolytic anemia after childhood *Escherichia coli* 1057:H7 infection: Are females at increased risk?" Epidemiol. Infect., 106:523–530 (1991).

Byrnes, J.J. & Moake, J.L., "TPP and HUS syndrome: Evolving concepts of pathogenesis and therapy," Clin. Hematol., 15:413–442 (1986).

Cleary, T.G., "Cytotoxin producing *Escherichia coli* and the hemolytic uremic syndrome," Pediatr. Clin. North Am., 35:485–501 (1988).

Gray, L.D., "Escherichia, Salmonella, Shigella, and Yersinia," in *Manual of Clinical Microbiology*, 6th edition, P. Murray et al. (eds), ASM Press, Washington, D.C., pp. 450–456 (1995).

Dufour, A.P., "*E. coli:* the fecal coliform," in *Bacterial Indicators/Health Hazards Associated with Water*, A.W. Hoadley and B.J. Dutka (eds.), ASTM, Philadelphia, pp. 48–58 (1976).

Cabelli, V.J., "Health effects criteria for marine recreational waters," EPA–600/1–80–031, pp. 11–12 (Aug., 1983).

Raghubeer, E.V. & Matches, J.R., "Temperature range for growth of *Escherichia coli* serotype 0157:H7 and selected coliforms in *E. coli* medium," J. Clin. Microbiol., 28: 803–805 (1990).

Doyle, M.P. & Schoeni, J.L., "Survival and growth characteristics of *Escherichia coli* associated with hemorrhagic colitis," Appl. Environ. Microbiol., 48:855–856 (1984).

Kehr, R.W. & Butterfield, C.T., "Notes on the relationship between coliforms and enteric pathogens," Public Health Repts., 58:589–607 (1943).

Batik, O., et al., "Routine coliform monitoring and waterborne disease outbreaks," J. Environ. Health 45:227–230 (1984).

American Public Health Association—American Water Works Association—Water Pollution Control Federation, *Standard methods for the examination of water and wasterwater*, 16th Ed., APHA, Washington, D.C., (1985).

Reasoner, D.J. & Geldreich, E.E., "Rapid detection of water–borne fecal coliforms by $^{14}CO_2$ release," in *Mechanizing Microbiology*, A.N. Sharpe and D.S Clark (eds.), Charles C. Thomas Publishers, pp. 120–139 (1978).

Dange, V., et al., "One hour portable test for drinking waters," Water Res., 22:133–137 (1988).

Frampton, E.W., et al., "Evaluation of the β–glucuronidase substrate 5–bromo–4–chloro–3–indolyl–β–glucuronide (X–GLUC) in a 24–hour direct plating method for *Escherichia coli*," J. Food Protect., 51:402–404 (May 1988).

Restaino, L., et al.,"Use of the chromogenic substrate 5–bromo–4–chloro–3–indolyl–β–D–glucuronide (X–GLUC) for enumerating *Escherichia coli* in 24 H from ground beef," J. Food Protect., 53:508–510 (1990).

Frampton, E.G. & Restaino, L., "Methods for *Escherichia coli* identification in food, water and clinical samples based on beta–glucuronidase detection," J. Appl. Bacteriol., 74:223–233 (1993).

Chang, G.W., et al., "Proportion of β–D–glucuronidase–negative *Escherichia coli* in human fecal samples," Appl. Environ. Microbiol., 55:335–339 (1989).

Wentsel, R.S., et al., "Evaluation of coliphage detection as a rapid indicator of water quality," Appl. Environ. Microbiol., 43:430–434 (1982).

Kott, Y., et al., "Bacteriophages as bacterial viral pollution indicators," Water Res., 8:165–71 (1982).

Havelaar, A.H., et al., "Factors effecting the enumeration of coliphages in sewage and sewage polluted waters," Antonie van Leewenhoek 49:387–397 (1983).

Padhye, N.V. & Doyle, M.P., "Rapid procedure for detecting enterohemmorrhagic *Escherichia coli* 0157:H7 in food," Appl. Environ. Microbiol., 57:2693–2698 (1991).

Isenberg, H.D. & D'Amato, R.F., "Indigenous and Pathogenic Microorganisms of Humans," in *Manual of Clinical Microbiology*, 6th edition, P. Murray et al. (eds.), ASM Press, Washington, D.C., p.9 (1995).

Koneman, E.G., et al., *Color Atlas and Textbook of Diagnostic Microbiology*, 4th ed., J.B. Lippincott Co., Philadelphia, p. 119 (1992).

Grasmick, A., "Processing and Interpretation of Bacterial Fecal Cultures," in Section 1, Aerobic Bacteriology, in *Clinical Microbiology Procedures Handbook*, H. Isenberg (ed.), American Society for Microbiology, Washington, D.C., p. 1.10.5, (1994).

March, S.B. & Ratnam, S., "Sorbitol–MacConkey medium for detection of *Escherichia coli* 0157:H7 associated with hemorrhagic colitis," J. Clin. Microbiol., 23:869–872 (1986).

"More fall meeting highlights," NCASM Winter Newsletter, p.4 (1994).

Fratamico, P.M., et al., "Virulence of an *Escherichia coli* 0157:H7 sorbitol–positive mutant," Appl. and Environ. Microbiol., 59:4245–4252 (1993).

Ritchie, M., et al., "Comparison of a direct fecal shiga–like toxin assay and sorbitol MacConkey agar culture for laboratory diagnosis of enterohemorrhagic *Escherichia coli* infection," J. Clin. Microbiol., 30:461–464 (1992).

Thompson, J.S., et al., "Rapid biochemical test to identify verocytotoxin–positive strains of *Escherichia coli* serotype 0157," J. Clin. Microbiol., 28:2165–2168 (1990).

Okrend, A.J.G., et al., "Use of 5–bromo–4–chloro–3–indoxyl–β–D–glucuronide in SMAC to aid in the isolation of *Escherichia coli* 0157:H7 from ground beef," J. Food Protect., 53:941–943 (1990).

Niroomand, F. & Lord, C., "Comparison of Rapid Techniques for the detection of *Escherichia coli* 0157:H7," J. Rapid Meth. Automation Microbiol., 3:85–96 (1994).

Chapman, P.A., et al., "An improved selective medium for the isolation of *Escherichia coli* 0157," J. Med. Microbiol., 35:107–110 (1991).

Abbott, S.L., et al., "*Escherichia coli* 0157:H7 generates a unique biochemical profile on MicroScan conventional gram–negative identification panels," J. Clin. Microbiol., 32:823–824 (1994).

Zadik, P.M., et al., "Use of tellurite for the selection of verocytotoxigenic *Escherichia coli* 0157," J. Med. Microbiol., 39:155–158 (1993).

Szabo, R.A. et al., "Method to isolate *Escherichia coli* 0157:H7 from food," J. Food Protect., 49:768–772 (1986).

Farmer, J.J. & Davis, B.R., "H7 antiserum–sorbitol fermentation medium: A single tube screening medium for detecting *Escherichia coli* 0157:H7 associated with hemorrhagic colitis," J. Clin. Microbiol., 22:620–625 (1985).

Okrend, A.J.G., et al., "A screening method for the isolation of *Escherichia coli* 0157:H7 from ground beef," J. Food Protect., 53:249–252 (1990).

Kim, M.S. & Doyle, M.P., "Dipstick immunoassay to detect enterohemorrhagic *Escherichia coli* 0157:H7 in retail ground beef," Appl. Environ. Microbiol., 58:1764–1767 (1992).

Gannon, V.P.J., et al., "Rapid and sensitive method for the detection of Shiga–like toxin–producing *Escherichia coli* in ground beef using the polymerase chain reaction," Appl. Environ. Microbiol., 58:3809–3815 (1992).

Jackson, M.P., "Detection of Shiga toxin–producing *Shigella dysenteriae* type 1 and *Escherichia coli* using the polymerase chain reaction with incorporation of digoxigenin–11–dUTP," J. Clin. Microbiol., 29:1910–1914 (1991).

Johnson, W.M., et al., "Amplification by the polymerase chain reaction of a specific target sequence in the coding for *Escherichia coli* verotoxin (Vte) variant," FEMS Microbiol., 84:227–230 (1991).

Karch, H. & Meyers, T., "Single primer pair for amplifying segments of distinct Shiga–like toxin genes by polymerase chain reaction," J. Clin. Microbiol., 287:2751–2757 (1989).

Dusch, H., and Altwegg, M., "Evaluation of five new plating media for isolation of Salmonella species," J. Clin. Microbiol., 33:802–804 (1995).

Poisson, D.M., "Novobiocin, brilliant green, glycerol lactose sugar: A new medium for the isolation of Salmonella strains," Res. Microbiol., 143:211–216 (1992).

Rambach, A., "New plate medium for facilitated differentiation of Salmonella spp. from Proteus spp. and other enteric bacteria," Appl. Environ. Microbiol., 56:301–303 (1990).

Cox, J.M., "Lysine–mannitol–glycerol agar, a medium for the isolation of Salmonella, including *S. typhi* and atypical strains," Appl. Environ. Microbiol., 59:2602–2606 (1993).

Stallard, K.R. & Cox, J.M., "Lysine mannitol glycerol agar (LMG) with sulphamanadelate for isolation of Salmonella spp. from clinical specimens," Lett. Appl. Microbiol., 19:83–87 (1994).

Rosenberg, M., "Initial testing of a novel urine culture device," J. Clin. Microbiol., 30:2686–2691 (1992).

Dalet, F. & Segovia, T., "Evaluation of a new agar in Uricult–trio for rapid detection of *Escherichia coli* in urine" J. Clin. Microbiol., 33:1395–1398 (1995).

Doyle, M.P., & Schoeni, J.L., "Isolation of *Escherichia coli* 0157:H7 from retail fresh meats and poultry," Appl. Environ. Microbiol., 53:2394–2396 (1987).

Okrend, A.J.G., et al., "An improved screening method for the detection and isolation of *Escherichia coli* 0157:H7 from meat, incorporating the 3M Petrifilm™ test kit—HEC—for hemorrhagic *Escherichia coli* 0157:H7," J. Food Protect., 11:936–940 (1990).

Sepúlveda, J.L., et al., "Rapid presumptive identification of Gram–negative rods directly from blood cultures by simple enzymatic tests," J. Clin. Microbiol., 28:177–181 (1990).

Freydiere, A–M. & Gillie, Y., "Detection of Salmonellae by using Rambach agar and by a C8 esterase spot test," J. Clin. Microbiol., 29:2357–2359 (1991).

Lior, H., "*Escherichia coli* 0157:H7 and verotoxigenic *Escherichia coli* (VTEC)," Dairy, Food and Environ. Sanitation 14:378–382 (1994).

Haldane, D.J.M., et al., "Improved biochemical screening procedure for small clinical laboratories for Vero (Shiga–like)–toxin–producing strains of *Escherichia coli* 0157:H7," J. Clin. Microbiol., 24:652–653 (1986).

Ratnam, S., et al., "Characterization of *Escherichia coli* serotype O157:H7," J. Clin. Microbiol., 26:2006–2012 (1988).

Perry, M., et al., "Identification of *Escherichia coli* serotype O157 strains by using a monoclonal antibody," J. Clin. Microbiol., 26:2391–2394 (1988).

March, S.B. & Ratnam, S., "Latex agglutination test for detection of *Escherichia coli* serotype O157," J. Clin. Microbiol., 27:1675–1677 (1989).

Maniar, A.C., et al., "Detection of verotoxin in stool specimens," J. Clin. Microbiol., 28:134–135 (1990).

Tison, D., "Culture confirmation of *Escherichia coli* serotype O157:H7 by direct immunofluorescence," J. Clin. Microbiol., 28:612–613 (1990).

Padhye, N.V. & Doyle, M.P., "Production and characterization of a monoclonal antibody specific for enterohemorrhagic *Escherichia coli* of serotypes O157:H7 and O26:H11," J. Clin Microbiol., 29:99–103 (1991).

Wells, J.G., et al., "Isolation of *Escherichia coli* serotype O157:H7 and Shiga–like–toxin–producing *E. coli* from dairy cattle," J. Clin. Microbiol., 29:985–989 (1991).

Bitzan, M. & Karch, H., "Indirect hemagglutination assay for diagnosis of *Escherichia coli* O157 infection in patients with hemolytic–uremic syndrome," J. Clin. Microbiol., 30:1174–1178 (1992).

Rice, E.W., et al., "Serological cross–reactions between *Escherichia coli* O157 and other species of the genus Escherichia," J. Clin. Microbiol., 30:1315–1316 (1992).

Brian, M.J., et al., "Polymerase chain reaction for diagnosis of enterohemorrhagic *Escherichia coli* infection and hemolytic–uremic syndrome," J. Clin. Microbiol., 30:1801–1806 (1992).

Gunzer, F., et al., "Molecular detection of sorbitol–fermenting *Escherichia coli* O157 in patients with hemolytic–uremic syndrome," J. Clin Microbiol., 30:1807–1810 (1992).

Yamada, S., et al., "Serodiagnosis by passive hemagglutination test and verotoxin enzyme–linked immunosorbent assay of toxin–producing *Escherichia coli* infections in patients with hemolytic–uremic syndrome," J. Clin. Microbiol., 32:955–959 (1994).

Beutin, L., et al., "Virulence markers of Shiga–like toxin–producing *Escherichia coli* strains originating from healthy domestic animals of different species," J. Clin. Microbiol., 33:631–635 (1995).

Stacy–Phipps, S., et al., "Multiplex PCR assay and simple preparation method for stool specimens detect enterotoxigenic *Escherichia coli* DNA during course of infection," J. Clin. Microbiol., 33:1054–1059 (1995).

Law, D., et al., "Detection of ELISA of low numbers of Shiga–like toxin–producing *Escherichia coli* in mixed cultures after growth in the presence of mitomycin C," J. Med. Microbiol., 36:198–202 (1992).

Chapman, P.A., et al., "A comparison of immunomagnetic separation and direct culture for the isolation of verocytotoxin–producing *Escherichia coli* O157 in bovine faeces," J. Med. Microbiol., 40:424–427 (1994).

Todd, E.C.D., et al., "Rapid hydrophobic grid membrane filter–enzyme–labeled antibody procedure for identification and enumeration of *Escherichia coli* O157 in foods," Appl. Environ. Microbiol., 54;2536–2540 (1988).

Szabo, R., et al., "Increased Sensitivity of the Rapid Hydrophobic Grid Membrane Filter Enzyme–Labeled Antibody Procedure for *Escherichia coli* O157 Detection in Foods and Bovine Feces," Appl. Environ. Microbiol., 56:3546–3549 (1990).

Feng, P., et al., "Genetic analysis of uidA expression in enterohaemorrhagic *Escherichia coli* serotype O157:H7," Microbiology 140:2101–2107 (1994).

The American Digestive Health Foundation, "Consensus conference statement *E. coli* O157:H7 infections: An emerging national health crisis," Jul. 11–13, 1994.

Sullivan, N., "Introducing *EZ Coli* for detection of *Escherichia coli* O157 from food," in *Culture Club News,* vol. 4 (Spring/Summer 1995), published by Difco Laboratories.

Nakamura et al., Proc. Mout. Acad. Sci, 28 Annual Meeting, 1968, p. 51–57.

Narasimhan et al., *Indian Vet. J.,* vol. 66, p. 51–55, 1989.

Jeter, R.M., *J. of Gen. Microbiol.,* vol. 136, p. 887–896.

Kolodziej et al, Arch Biochem. Biophys, 123, 66–71, 1968.

Wegener et al, Arch. Biochem. Biophys, 123, 62–65, 1968.

Tortora et al, "Microbiology", Benjamin Cummings Publ. Co. 1995.

Atlas et al. "Microbiological Media", CRC 1994, p. 178–179 and 819.

MICROBIOLOGICAL MEDIA FOR ISOLATION AND INDENTIFICATION OF ENTERIC PATHOGENS SUCH AS *E. COLI* AND SALMONELLA

This is a continuation of copending application Ser. No. 08/484,960 filed Jun. 7, 1995.

FIELD OF THE INVENTION

The present invention relates to culture media useful for rapid screening of clinical and environmental cultures to detect some of the most common bacterial pathogens. The reactions observed on these media are useful for rapid and cost-effective presumptive diagnosis of infection due to various bacteria, or screening of food and water samples to prevent infection. Although many additional applications are contemplated, these media are particularly useful for testing samples which may contain enteric organisms such as *E. coli* and Salmonella species.

BACKGROUND OF THE INVENTION

An ever-enlarging world population has increased demands on water and food resources worldwide. Indeed, this population increase is directly proportional to the potential for surface and ground water contamination by pathogenic organisms associated with increased waste burdens. In addition, modern high-output production of meat and other foods represents significant sources of food-borne illnesses. To ensure good public health, there is a need for readily available methods to detect and enumerate pathogens in water, feed, and food. Unfortunately, despite years of testing and research, no single procedure is available for the reliable detection of the major waterborne and foodborne pathogens. Indeed, there are no standardized methods for detecting all of the important pathogens associated with food and waterborne disease. The methods that are available are usually time-consuming and expensive.

I. Gastrointestinal Diseases

Despite advances in public health technology, water and food remain important reservoirs of diarrheal and other diseases of humans and other animals. Infectious diarrhea among children (especially those under 5 years of age), the elderly housed in nursing homes, and travellers visiting developing countries represents a significant public health concern. According to one estimate, infectious diarrhea results in the hospitalization of 200,000 children in the United States each year, at an annual cost of one billion dollars (M. Ho et al., "Rotavirus as a cause of diarrheal morbidity and mortality in the United States," J. Infect. Dis., 158:1112–1116, 1988).

A. Water-Borne Disease

Worldwide, waterborne disease is of even greater significance, with over 250 million reported cases of waterborne disease and more than 10 million deaths annually (J. D. Snyder and M. H. Merson, "The magnitude of the global problem of acute diarrheal disease: a review of active surveillance data," Bull. World Health Organ., 60:605–613 [1982]). When other sources of diarrheal disease are taken into consideration the figures are even more staggering, with these diseases claiming the lives of over 5 million children per year in developing countries (T. L. Hale, "Genetic basis of virulence in Shigella species," Microbiol. Rev., 55:206–224 [1991]).

Most of the cases of waterborne diarrheal disease result from the contamination of drinking water supplies with human fecal material. Contamination of ground water in local areas may occur through such mechanisms as seepage of sewage into aquifers and by improperly developed or poorly protected wells. When factors such as recreational exposure to contaminated salt and fresh water are also taken into consideration, diarrheal disease takes on even greater importance.

Various infectious agents are associated with human waterborne diseases, including Campylobacter, *E. coli*, Leptospira, Pasteurella, Salmonella, Shigella, Vibrio, Yersinia, Proteus, Giardia, Entoamoeba, Cryptosporidium, hepatitis A virus, Norwalk, parvovirus, polio virus, and rotavirus. Worldwide, the most common bacterial diarrheal diseases are associated with waterborne transmission of Shigella, Salmonella, pathogenic *E. coli*, *Campylobacter jejuni*, and *Vibrio cholerae* (Singh and McFeters, "Detection methods for waterborne pathogens," pp. 125–156, in R. Mitchell (ed.), Environmental Microbiology, [Wiley-Liss, New York, 1992]). Table 1 lists important characteristics of diseases associated with a few of the most significant organisms.

TABLE 1

Waterborne Diarrheal Bacterial Diseases Most Commonly Reported

| Organism | Disease | Incubation Period | Common Symptoms |
| --- | --- | --- | --- |
| Shigella sp. | Shigellosis | 1–7 days | Diarrhea, fever, cramps, tenesmus, dysentery* |
| Salmonella | Salmonellosis | 6–72 hours | Abdominal pain, diarrhea, nausea, vomiting, fever |
| S. typhi | Typhoid fever | 1–3 days | Abdominal pain, fever, chills, diarrhea or constipation, intestinal hemorrhage |
| Pathogenic E. coli | Diarrhea | 12–72 hours | Diarrhea, fever, vomiting* |
| Campylobacter jejuni | Gastroenteritis | 1–7 days | Abdominal pain suggesting acute appendicitis, fever, headache, malaise, diarrhea, vomiting |
| Proteus sp. | Scombroid fish poisoning | Few minutes to 1 hour | Headache, dizziness, vomiting, nausea, peppery taste, burning throat, facial swelling and flushing, stomach pain, itching |
| Yersinia enterocolitica | Yersiniosis | 24–36 hours | Severe abdominal pain, fever, headache |
| Vibrio parahaemolyticus | | 12 hours | Vomiting, diarrhea, abdominal pain, fever |
| Vibrio cholerae | Gastroenteritis | 1–3 days | Vomiting, diarrhea, dehydration |

*Additional symptoms and sequelae are discussed below.

Swimming-associated outbreaks caused by Shigella, Giardia, Norwalk-like viruses, and other enteroviruses have been well documented (See e.g., Makintubee et al., "Shigellosis outbreak associated with swimming," Am. J. Public Health 77:166–168 [1987]; F. J. Sorvillo et al., Shigellosis associated with recreational water contact in Los Angeles County," Am. J. Trop. Med. Hyg., 38:613–617 [1988]).

The following table lists the majority of waterborne infectious bacteria which are associated with human diarrheal and non-diarrheal disease.

TABLE 2

Infectious Bacteria Transmitted by Water

| Organism | Commonly Associated Diseases in Humans |
| --- | --- |
| Acinetobacter calcoaceticus | Nosocomial infections |
| Aeromonas hydrophila | Enteritis, wound infections |
| A. sobria | |
| A. caviae | |
| Campylobacter jejuni | Enteritis |
| C. coli | |
| Chromobacterium violaceum | Enteritis |
| Citrobacter spp. | Nosocomial infections |
| Clostridium perfringens, type C | Enteritis |
| Enterobacter spp. | Nosocomial infections |
| E. coli, various serotypes | Enteritis** |
| Flavobacterium meningosepticum | Nosocomial infections, meningitis |
| Francisella tularensis | Tularemia |
| Fusobacterium necrophorum | Liver abscesses |
| Klebsiella spp. | Nosocomial infections, pneumonia |
| Leptospira icterohaemorrahagia and other Leptospira spp. | Leptospirosis |
| Legionella pneumophiia and other Legionella spp. | Legionellosis |
| Morganella morganii | Urethritis, nosocomial infections |
| Mycobacterium tuberculosis | Tuberculosis |
| M. marinum and other Mycobacterium spp. | Granuloma, dermatitis |
| Plesiomonas shigelloides | Enteritis |
| Pseudomonas pseudomallei | Melioidosis |
| Pseudomonas spp. | Dermatitis, ear infections |
| Salmonella enteritidis | Enteritis (salmonellosis) |
| S. montevideo B | |
| S. typhimurium and other Salmonella serotypes | |
| S. paratyphi A and B | Paratyphoid fever |
| S. typhi | Typhoid fever |
| Serratia marcesens | Nosocomial infections |
| Shigella spp. | Dysentery |
| Staphylococcus aureus | Wounds, food poisoning |
| Vibrio cholerae | Cholera |
| V. alginolyticus | Enteritis |
| V. fluvialis | Wound infections |
| V. mimicus | |
| V. parahaemolyticus | |
| V. vulnificus | |
| Other Vibrio spp. | |
| Yersinia enterocolitica | Enteritis |

*After T. C. Hazen and G. A. Toranzos, "Tropical Source Water," p. 33, in G. A. McFeters, Drinking Water Microbiology [Springer-Verlag, New York, 1990].
**Additional diseases and sequelae are discussed below.

While the presence of pathogens in drinking and recreational waters presents a significant public health concern, recovery of pathogens from environmental samples is generally difficult. In addition to the usually low numbers of organisms present in the water, nutrient limitations and environmental stressors produce unpredictable physiological and morphological changes in these pathogens. This makes their recovery, isolation and identification problematic. Organisms injured due to these environmental stressors often exhibit atypical reactions and require specialized handling for their resuscitation (see e.g., Singh and McFeters, p. 132–133).

Routine or periodic monitoring of water for the presence of pathogens is essential in situations such as wastewater reclamation, during and after waterborne outbreaks, and for water sources with a frequent history of contamination. This is largely due to the observation that most enteric pathogens appear intermittently and in low concentrations in aquatic environments. Thus, potentially pathogenic organisms may be present in a water supply and go undetected, largely due to their low numbers and the limitations of current testing methods, including relatively low sensitivity levels.

Often, organisms are present but are unculturable (Singh and McFeters, at 131–159; see also, J. J. Byrd et al., "Viable but nonculturable bacteria in drinking water," Appl. Environ. Microbiol., 57:875–878 [1991]; C. Desmonts et al., "Fluorescent-antibody method useful for detecting viable but nonculturable Salmonella spp. in chlorinated wastewater," Appl. Environ. Microbiol., 56:1448–1442 [1990]; and J. J. Byrd and R. R. Colwell, "Maintenance of plasmids pBR322 and pUC8 in nonculturable Escherichia coli in the marine environment," Appl. Environ. Microbiol., 56:2104–2107 [1990]). Unless other methods are used for their detection (e.g., immunoassays) these viable, but nonculturable organisms may present an undetected threat to public health. In addition, the methods commonly used to detect these pathogens were initially designed for clinical, rather than environmental samples. This is of significance in view of the different ecological niche occupied by clinical as compared with environmental isolates. Clinical isolates are usually provided needed nutrients by their host animal and are generally protected from harsh environmental conditions such as cold, heat, damaging chemicals and radiation. In contrast, environmental isolates must deal with these environmental conditions and effectively compete with organisms naturally present and adapted to life in the environment.

B. Food-Borne Disease

In addition to water, food represents an important source of pathogens for humans and other animals. Food-borne illnesses represent an important cause of morbidity, mortality and economic loss in the United States, as well as other countries. Recent estimates by the U.S. Department of Agriculture (USDA) indicate that bacteria are responsible for 3.6 to 7.1 million cases of food-borne illness annually, with associated medical costs and productivity losses of $2.9 to 7.1 billion (J. G. Morris, "Watching the birds (and the beef): New approaches to meat and poultry inspection," ASM News 61:56–57 [1995]). Costs to affected individuals include medical bills, time lost from work, pain and inconvenience. Costs to the food industry include possible product recalls, closing and cleaning of food processing establishments, higher premiums for product liability insurance, loss of product reputation and reduced demand. Approximately $300 million/year is spent by the Federal public health sector on microbial food-borne diseases; federal costs average about $200,000 per food-borne illness outbreak (USDA, "Pathogen Reduction; Hazard Analysis and Critical Control Point (HACCP) Systems," Federal Register Part II 60(023):6774 (Friday, Feb. 3, 1995); hereinafter "USDA").

Food handling from harvest or slaughter to consumption provides numerous opportunities for contamination with pathogenic microorganisms. In the early 1890's, recognition of potential safety problems associated with meat led to enactment of inspection laws in Europe and the United States. These laws have undergone periodic revision and federal laws to protect the food supply are currently in force. Indeed, the laws require that inspected meat and poultry products bear an official inspection legend. Presently, more than 7,300 inspectors from the Food Safety and Inspection Service (FSIS) of the USDA enforce the inspection laws in approximately 6,2000 meat and poultry establishments. Inspection activities start prior to slaughter and continue through processing, handling and packaging. Of the 129,831,110 meat-animal carcasses inspected during fiscal year 1993, 384,543 (0.3%) were condemned for disease, contamination or adulteration during the inspection process. Of the 7,085,491,852 poultry carcasses inspected this same year, 63,926,693 (0.9%) were condemned (USDA, at 6780).

Unsanitary practices and working conditions (e.g., in slaughterhouses), as well as improper storage and preparation procedures contribute greatly to the risk of contamination. For example, at least seventy pathogens have been identified among the organisms isolated from animals at slaughterhouses (J. G. Black, *Microbiology Principles and Applications,* 2d edition, Prentice Hall, New Jersey, [1993] p. 751). In many areas of the United States, poultry and eggs are commonly contaminated with Salmonella. Over twenty bacterial genera have been isolated from dressed poultry, and improperly handled poultry accounts for many cases of foodborne disease. Half of the infections associated with consumption of improperly handled poultry obtained at restaurants are due to Salmonella, while one-fourth are due to *Clostridium perfringens,* and the remaining one-fourth are due to *S. aureus* (Black at p. 751–752). This is of particular concern when the large number of birds slaughtered annually is taken into consideration (over 6 billion chickens and turkeys are slaughtered in the U.S. each year (USDA, "Pathogen Reduction; Hazard Analysis and Critical Control Point (HACCP) Systems," Federal Register Part II 60(023):6774 (Friday, Feb. 3, 1995)). In a study conducted in 1990–1992, approximately 25% of raw products, including broiler chickens were contaminated with Salmonella. In a study on ready-to-cook raw beef conducted from January 1987 through March 1990, the prevalence of Salmonella in 25 gram samples was found to be 1.6%, the prevalence of Listeria was 7.1%, and the prevalence of *E. coli* 0157:H7 was 0.1%. In a 1992 study of heifer and steer carcasses, *C. perfringens* was recovered from 2.6% of 2,079 carcasses, *C. jejuni/coli* was recovered from 4% of 2,064 carcasses, *S. aureus* was recovered from 4.2% of 2,089 carcasses, *E. coli* 0157:H7 was recovered from 0.2% of 2,081 carcasses, and Salmonella was recovered from 1% of 2,089 carcasses.

It has been estimated that food-borne pathogens account for up to 7 million cases of food-borne illness annually in the U.S., and up to 7,000 deaths. Of these, almost 5 million cases of foodborne illness and more than 4,000 deaths may be associated with meat and poultry products contaminated with pathogens (USDA, at 6781–6782). However, these estimates may be too low. The following table lists selected food-borne pathogens (including one protozoan parasite, *Toxoplasma gondii*), the number of cases which were reported in 1993, and estimates of the associated costs. The USDA Economic Research Service and the Centers for Disease Control (CDC) estimate that the cost of all of all food-borne illness in the U.S. in 1993 to have been between $5.6 and $9.4 billion. Of these cases, meat and poultry products were associated with approximately $4.5 to $7.5 billion.

TABLE 3

Selected Food-Borne Pathogens

| Pathogen | Total Cases in 1993 | Total Deaths in 1993 | 1993 Food-borne Costs (bil $) | Percent from Meat/Poultry |
|---|---|---|---|---|
| *Campylobacter jejuni* or *C. coli* | 2,500,000 | 200–730 | 0.6–1.0 | 75 |
| *Clostridium perfringens* | 10,000 | 100 | 0.1 | 50 |
| *E. coli* 0157:H7 | 10,000–20,000 | 200–500 | 0.2–0.6 | 75 |
| *Listeria monocytogenes* | 1,795–1,860 | 445–510 | 0.2–0.3 | 50 |
| Salmonella | 800,000–4,000,000 | 800–4,000 | 0.6–3.5 | 50–75 |
| *Staphylococcus aureus* | 8,900,000 | 7,120 | 1.2 | 50 |
| *T. gondii* | 4,111 | 82 | 2.7 | 100 |

As illustrated by the above table, Salmonella was associated with a large percentage of food-borne illness cases and deaths. However, other organisms are also commonly associated with foodborne infection and disease. For example, many of the organisms listed in Table 1 above are associated with foodborne disease. The following Table lists the organisms most commonly isolated from cases of foodborne disease or infection, foods commonly associated with the organisms, and their reservoirs of infection. Additional organisms, such as the Helicobacter species are also associated with gastrointestinal disease (although the mode of acquisition and transmission of this genus is not clear).

TABLE 4

Foodborne Bacterial Diseases Most Commonly Reported

| Organism | Disease | Commonly Associated Food(s) | Reservoir of Infection |
|---|---|---|---|
| *Shigella* sp. | Shigellosis | Salads, shrimp, ice | Human |
| *Salmonella* sp. | Salmonellosis | Poultry, eggs, powdered milk, chocolate, sausage | Poultry, cattle, sheep, turtles, humans |
| *S. typhi* | Typhoid fever | Foods contaminated with feces of carriers | Humans |
| Pathogenic *E. coli* | Various | Soft cheese, ground meat | Various foods, infected humans and other animals |
| *Staphylococcus aureus* | Staphylococcal food intoxication | Cream-filled pastries, ham, pork, sausage | Nose, skin, and lesions on humans, udders of cattle |
| *Clostridium perfringens* | Gastroenteritis | Gravies, meat | Soil, humans |
| *C. botulinum* | Botulism | Canned foods, fish products, potatoes | Soil |
| *Bacillus cereus* | Gastroenteritis | Boiled and fried rice, custards, sauces, meatloaf, gravies | Soil |

TABLE 4-continued

Foodborne Bacterial Diseases Most Commonly Reported

| Organism | Disease | Commonly Associated Food(s) | Reservoir of Infection |
| --- | --- | --- | --- |
| Streptococcus pyogenes | Streptococcal infections | Raw milk, dairy products, salads, uncooked foods | Nose and throat of humans, infected sores |
| Listeria monocytogenes | Listeriosis | Raw milk, cheese, contaminated vegetables | Intestinal tract of humans and other animals, soil |
| Brucella spp. | Brucellosis | Raw milk, goat cheese | Cattle, pigs, sheep, goats |
| Campylobacter jejuni | Gastroenteritis | Foods of animal origin | Raw milk, poultry, beef, pork |
| Proteus spp. | Scombroid fish poisoning | Tuna, mackerel, mahi mahi | Humans, ice |
| Yersinia enterocolitica | Yersiniosis | Dairy products, meats | Cattle, ice |
| Vibrio parahaemolyticus | Gastroenteritis | Marine animals | Raw sea fish, shellfish |
| Vibrio cholerae | Gastroenteritis | Raw fish and shellfish grown in or washed with contaminated water | Fish and shellfish from contaminated water |
| Vibrio vulnificus and other Vibrio spp. | Wound infections, septicemia | Raw seafood, sea water | Seafood and seawater |
| Aeromonas spp. | Diarrhea, dysentery bacteremia, wound infections, endocarditis, meningitis, pneumonia, osteomyelitis, peritonitis, conjunctivitis, thrombophlebitis, cholecystitis | Dairy products, meats, produce, water, marine products | Meats, produce, dairy, marine environment |
| Plesiomonas shigelloides | Gastroenteritis | Freshwater, seafood, amphibians, reptiles | Seafood, water, amphibians, reptiles |
| Helicobacter pylori H. fennelliae H. cinaedi | Gastritis, ulcers, bacteremia, neonatal septicemia and meningitis, proctocolitis, proctitis | ? | ? |

While colonization of the gastrointestinal tract by pathogens occurs and may cause disease (e.g., bacillary dysentery due to Shigella, diarrhea due to Salmonella, typhoid, etc.), many of the bacterial diseases associated with the gastrointestinal tract are due to ingestion of pre-formed toxins present in foods (e.g., toxins produced by *Staphylococcus aureus, Bacillus cereus, Clostridium botulinum,* etc.). In addition, many organisms which have colonized the gastrointestinal tract produce toxins which cause the signs and symptoms of disease (e.g., cholera, antimicrobial-associated pseudomembranous colitis due to *Clostridium difficile,* etc). Thus, the type of disease experienced by a patient often mandates the type of specimen(s) collected and the timing of such collections. Recently, some serotypes of *E. coli,* normally a harmless commensal resident in the intestinal tract of mammals have been recognized as important pathogens.

Concern over food safety largely due to recent outbreaks such as the salmonellosis outbreak associated with contaminated ice cream in Minnesota and the *E. coli* 0157:H7 outbreaks associated with fast food restaurants has lead to recent USDA Food Safety and Inspection Service (FSIS) proposals to implement a hazard analysis and critical control point (HACCP) strategy to assure safety of poultry and other meat (USDA, "Pathogen Reduction; Hazard Analysis and Critical Control Point (HACCP) Systems," Federal Register Part II 60(023):6774 (Friday, Feb. 3, 1995) (See J. L. Fox, "USDA's food-safety push boosts assay makers," Bio/Technol., 13:114–115, [1995]). These proposed regulations represent a major change in the currently used inspection practices. If enacted, these regulations would require food producers to identify particular steps along the production path where problems such as microbial and chemical contamination of food is likely to occur. Once these "critical control points" are identified, this would permit the food producers to monitor their safety efforts and take appropriate measures to prevent or correct problems.

Of concern in development of new tests to monitor food safety is the lack of specificity associated with antibody-antigen recognition systems and the lack of sensitivity of amplification methods (J. L. Fox, at 115). In addition, some of the molecular tests are difficult to use and are not readily adaptable to the environmental setting. Thus, acceptance of such methods by food producers remains questionable. What is needed is a method which can provide rapid, accurate identification of specific pathogens such as *E. coli* 0157:H7 and Salmonella on the surface of raw food products, at a minimal cost.

C. Clinical Samples Associated With Diagnosis of Gastrointestinal Disease

In addition to food and water, clinical samples are commonly tested for the presence of these organisms. Indeed, the diagnosis of infectious disease has traditionally relied upon microbiological culture methods to identify the causative organism and determine the appropriate antimicrobial treatment. This has remained so despite recent advances in molecular and immunological diagnostics. While the development of rapid and automated methods has served to increase the efficiency of microbiological analysis, traditional quantitative culture methods remain critical for definitive diagnosis of urinary tract and other infections (E. J. Baron & S. Finegold, *Diagnostic Microbiology,* 8th ed., C. V. Mosby, [1990], p. 253).

With respect to the type of specimen, there are considerations related to the normal flora from which the pathogens must be differentiated. This is particularly true for fecal, rectal, vaginal, buccal and other samples which commonly contain a characteristic background flora. For other samples (e.g., food, milk, water, and environmental), background flora and other considerations must also be taken into account. This is especially important with *E. coli,* as it is a commensal intestinal organism that is routinely isolated from healthy individuals.

II. *Echerichia coli* as a Pathogenic Organism

*E. coli* is the organism most commonly isolated in clinical microbiology laboratories, as it is usually present as normal flora in the intestines of humans and other animals. It is also an important cause of intestinal, as well as extraintestinal infections. For example, in a 1984 survey of nosocomial infections in the United States, *E. coli* was associated with 30.7% of the urinary tract infections, 11.5% of the surgical wound infections, 6.4% of the lower respiratory tract infections, 10.5% of the primary bacteremia cases, 7.0% of the cutaneous infections, and 7.4% of the other infections (J.

J. Farmer and M. T. Kelly, "Enterobacteriaceae," in *Manual of Clinical Microbiology,* Balows et al.(eds), American Society for Microbiology, [1991], p. 365). Surveillance reports from England, Wales and Ireland for 1986 indicate that *E. coli* was responsible for 5,473 cases of bacteremia (including blood, bone marrow, spleen and heart specimens); of these, 568 were fatal. For spinal fluid specimens, there were 58 cases, with 10 fatalities (J. J. Farmer and M. T. Kelly, "Enterobacteriaceae," in *Manual of Clinical Microbiology,* Balows et al.(eds), American Society for Microbiology, [1991], p. 366). There are no similar data for United States, as these are not reportable diseases in this country.

Studies in various countries have identified certain serotypes (based on both the O and H antigens) that are associated with the four major groups of *E. coli* recognized as enteric pathogens. Table 5 lists common serotypes included within these groups. The first group includes the classical enteropathogenic serotypes ("EPEC"); the next group includes those that produce heat-labile or heat-stable enterotoxins ("ETEC"); the third group includes the enteroinvasive strains ("EIEC") that mimic Shigella strains in their ability to invade and multiply within intestinal epithelial cells; and the fourth group includes strains and serotypes that cause hemorrhagic colitis or produce Shiga-like toxins (or verotoxins) ("VTEC" or "EHEC" [enterohemorrhagic *E. coli*]).

TABLE 5

Pathogenic *E. coli* Serotypes

| Group | Associated Serotypes |
| --- | --- |
| Entero-toxigenic (ETEC) | O6:H16; O8:NM; O8:H9; O11:H27; O15:H11; O20:NM; O25:NM; O25:H42; O27:H7; O27:H20; O63:H12; O78:H11; O78:H12; O85:H7; O114:H21; O115:H21; O126:H9; O128ac:H7; O128ac:H12; O128ac:H21; O148:H28; O149:H4; O159:H4; O159:H20; O166:H27; and O167:H5 |
| Entero-pathogenic (EPEC) | O26:NM; O26:H11; O55:NM; O55:H6; O86:NM; O86:H2; O86:H34; O111ab:NM; O111ab:H2; O111ab:H12; O111ab:H21; O114:H2; O119:H6; O125ac:H21; O127:NM; O127:H6; O127:H9; O127:H21; O128ab:H2; O142:H6; and O158:H23 |
| Entero-invasive (EIEC) | O28ac:NM; O29:NM; O112ac:NM; O115:NM; O124:NM; O124:H7; O124:H30; O135:NM; O136:NM; O143:NM; O144:NM; O152:NM; O164:NM; and O167:NM |
| Verotoxin-Producing (VTEC) | O1:NM; O2:H5; O2:H7; O4:NM; O4:H10; O5:NM; O5:H16; O6:H1; O18:NM; O18:H7; O25:NM; O26:NM; O26:H11; O26:H32; O38:H21; O39:H4; O45:H2; O50:H7; O55:H7; O55:H10; O82:H8; O84:H2; O91:NM; O91:H21; O103:H2; O111:NM; O111:H8; O111:H30; O111:H34; O113:H7; O113:H21; O114:H48; O115:H10; O117:H4; O118:H12; O118:H30; O121:NM; O121:H19; O125:NM; O125:H8; O126:NM; O126:H8; O128:NM; O128:H2; O128:H8; O128:H12; O128:H25; O145:NM; O125:H25; O146:H21; O153:H25; O157:NM; O157:H7; O163:H19; O165:NM; O165:19; and O165:H25 |

A. Verotoxin Producing Strains of *E. coli*

Although all of these disease-associated serotypes cause potentially life-threatening disease, *E. coli* O157:H7 and other verotoxin-producing strains have recently gained widespread public attention in the United States due to their recently recognized association with two serious extraintestinal diseases, hemolytic uremic syndrome ("HUS") and thrombotic thrombocytopenic purpura ("TTP"). Worldwide, *E. coli* O157:H7 and other verotoxin-producing *E. coli* (VTEC) are an increasingly important human health problem. First identified as a cause of human illness in early 1982 following two outbreaks of food-related hemorrhagic colitis in Oregon and Michigan (M. A. Karmali, "Infection by Verocytotoxin-Producing *Escherichia coli*," Clin. Microbiol. Rev., 2:15–38 [1989]; and L. W. Riley, et al. "Hemorrhagic colitis associated with a rare *Escherichia coli* serotype," New Eng. J. Med., 308: 681–685 [1983]), the reported incidence of VTEC-associated disease has risen steadily, with outbreaks occurring in the U.S., Canada, and Europe. In one nursing home outbreak in Canada, 55 elderly residents and 18 staff members were involved, and 17 residents (aged 78 to 99 years) died due to complications of hemorrhagic colitis (C. Krishnan et al., "Laboratory investigation of outbreak of hemorrhagic colitis caused by *Escherichia coli* O157:H7," J. Clin. Microbiol., 25:1043–1047 [1987]). This outbreak was notable for its relatively high fatality rate (approximately 31%).

With increased surveillance, *E. coli* O157:117 has been recognized in other areas of the world including Mexico, China, Argentina, Belgium, and Thailand (N. V. Padhye and M. P. Doyle, "*Escherichia coli* O157:H7: Epidemiology, pathogenesis and methods for detection in food," J. Food. Prot., 55: 555–565 [1992]; D. Piérard et al., "Results of screening for verocytotoxin-producing *Escherichia coli* in faeces in Belgium," Eur. J. Clin. Microbiol. Infect. Dis., 9:198–201 [1990]; and P. M. Griffin and R. V. Tauxe, "The epidemiology of infections caused by *Escherichia coli* O157:H7, other enterohemorrhagic *E. coli,* and the associated hemolytic uremic syndrome," Epidemiol. Rev., 13: 60 [1991]).

The disease attracted national attention in the U.S. after a major outbreak in the Pacific Northwest that was associated with consumption of undercooked *E. coli* O157:H7-contaminated hamburgers. Over 700 hundred people fell ill (more than 170 were hospitalized) and four young children died (P. I. Tarr, "Review of 1993 *Escherichia coli* O157:H7 outbreak: Western United States," Dairy Food & Environ. Sanitation 14:372–373 [1994]; and P. Recer, "Experts call for irradiation of meat to protect against food-borne bacteria," Associated Press, Jul. 12, 1994 [1994]). Several outbreaks since then have underscored the potential severity and multiple mechanisms for transmission of VTEC-associated diseases (M. Bielaszewská et al., "Verotoxigenic (enterohaemorrhagic) *Escherichia coli* in infants and toddlers in Czechoslovakia," Infection 18: 352–356 [1990]; A. Caprioli et al., "Hemolytic-uremic syndrome and Vero cytotoxin-producing *Escherichia coli* infection in Italy, " J. Infect. Dis., 166: 184–158 [1992]; A. Caprioli et al., "Community-wide Outbreak of Hemolytic-Uremic Syndrome Associated with Non-O157 Verocytotoxin-Producing *Escherichia coli*," J. Infect. Dis., 169: 208–211 [1994]; N. Cimolai, "Low frequency of high level Shiga-like toxin production in enteropathogenic *Escherichia coli* serogroups," Eur. J. Pediatr., 151: 147 [1992]; J. G. Wells, "Laboratory investigation of hemorrhagic colitis outbreaks associated with a rare *Escherichia coli* serotype," J. Clin. Microbiol., 18:512–520 [1983]; and R. Voelker, "Panel calls *E. coli* screening inadequate," *Escherichia coli* O157:H7— Panel sponsored by the American Gastroenterological Association Foundation in July 1994, Medical News & Perspectives, J. Amer. Med. Assoc., 272: 501 [1994]). One 1990 outbreak of interest to those responsible for water quality was associated with water-borne transmission due to freeze-fracture of municipal water pipes. This outbreak required two months to control, was quite large, and notable for its severity, with two HUS cases and four deaths (reviewed by MA. Neill, "*E. coli* O157:H7 time capsule: What do we know and when did we know it?," Dairy Food & Environ. Sanitation 14:374–377 [1994]).

While O157:H7 is currently the predominant *E. coli* serotype associated with illness in North America, other serotypes (as shown in Table 1, and in particular O26:H11, O113:H21, O91:H21 and O111:NM) also produce verotoxins which appear to be important in the pathogenesis of gastrointestinal manifestations and the hemolytic uremic syndrome (P. M. Griffin and R. V. Tauxe, "The epidemiology of infections caused by *Escherichia coli* O157:H7, other enterohemorrhagic *E. coli,* and the associated hemolytic uremic syndrome," Epidemiol. Rev., 13: 60 [1990]; M. M. Levine et al., "Antibodies to Shiga holotoxin and to two synthetic peptides of the B subunit in sera of patients with Shigella dysenteriae 1 dysentery," J. Clin. Microbiol., 30: 1636–1641 [1992]; J. R. Molenda et al.,*"Escherichia coli* (including 0157:H7): An environmental health perspective," Dairy Food & Environ. Sanitation 14:742–747 [1994]; and C. R. Dorn et al., "Properties of Vero cytotoxin producing *Escherichia coli* of human and animal origin belonging to serotypes other than O157:H7," Epidemiol. Infect., 103: 83–95 [1989]). Since organisms with these serotypes have been shown to cause illness in humans they may assume greater public health importance over time (P. M. Griffin and R. V. Tauxe, "The epidemiology of infections caused by *Escherichia coli* O157:H7, other enterohemorrhagic *E. coli,* and the associated hemolytic uremic syndrome," Epidemiol. Rev., 13: 60 [1990]).

Clinicians usually observe cases of hemolytic uremic syndrome ("HUS") clustered in a geographic region. However, small outbreaks are likely to be missed because many laboratories do not routinely screen stool specimens for *E. coli* O157:H7. Many cases related to non-commercial food preparation also probably go unrecognized. Nonetheless, *E. coli* O157:H7 is responsible for a large number of cases, as more than 20,000 cases of *E. coli* O157:H7 infection are reported annually in the U.S., with 400–500 deaths from HUS. However, these estimates were compiled when only 11 states mandated reporting of *E. coli* O157:H7. Twenty-nine states have recently made *E. coli* O157:H7 infection a reportable disease (R. Voelker, "Panel calls *E. coli* screening inadequate; *Escherichia coli* O157:H7; panel sponsored by the American Gastroenterological Association Foundation in July 1994, Medical News & Perspectives," J. Amer. Med. Assoc., 272: 501 [1994]). Indeed, the Centers for Disease Control recently added *E. coli* O157:H7 to their list of reportable diseases ("Public Health Threats," Science 267:1427 [1995]), and is now recommending that all diarrheal specimens be examined for its presence.

B. Nature of Verotoxin-Induced Disease

Risk factors for HUS progression following infection with *E. coli* O157:H7 include age (very young or elderly), bloody diarrhea, leukocytosis, fever, large amounts of ingested pathogen, previous gastrectomy, and the use of antimicrobial agents (in particular, trimethoprim-sulfamethoxazole)(A. A. Harris et al., "Results of a screening method used in a 12 month stool survey for *Escherichia coli* O157:H7," J. Infect. Dis., 152: 775–777 [1985]; and M. A. Karmali, "Infection by Verocytotoxin-producing *Escherichia coli,*" Clin. Microbiol. Rev., 2: 15–38 [1989]).

As indicated above, *E. coli* O157:H7 is associated with significant morbidity and mortality. The spectrum of illness associated with *E. coli* O157:H7 infection includes asymptomatic infection, mild uncomplicated diarrhea, hemorrhagic colitis, HUS, and TTP". Hemorrhagic colitis (or "ischemic colitis") is a distinct clinical syndrome characterized by sudden onset of abdominal cramps—likened to the pain associated with labor or appendicitis—followed within 24 hours by watery diarrhea. One to two days later, the diarrhea turns grossly bloody in approximately 90% of patients and has been described as "all blood and no stool" (C. H. Pai et al., "Sporadic cases of hemorrhagic colitis associated with *Escherichia coli* O157:H7," Ann. Intern. Med., 101: 738–742 [1984]; and R. S. Remis et al., "Sporadic cases of hemorrhagic colitis associated with *Escherichia coli* O157:H7," Ann. Intern. Med., 101: 738–742 [1984]). Vomiting may occur, but there is little or no fever. The time from ingestion to first loose stool ranges from 3–9 days (with a mean of 4 days) L. W. Riley et al., "Hemorrhagic colitis associated with a rare *Escherichia coli* serotype," New Eng. J. Med., 308: 681–685 [1983]; and D. Pudden et al., "Hemorrhagic colitis in a nursing home," Ontario Can. Dis. Weekly Rpt., 11: 169–170 [1985]), and the duration of illness ranges generally from 2–9 days (with a mean of 4 days).

HUS is a life-threatening blood disorder that appears within 3–7 days following onset of diarrhea in 10–15% of patients. Those younger than 10 years and the elderly are at particular risk. Symptoms include renal glomerular damage, hemolytic anemia (rupturing of erythrocytes as they pass through damaged renal glomeruli), thrombocytopenia and acute kidney failure. Approximately 15% of patients with HUS die or suffer chronic renal failure. Indeed, HUS is a leading cause of renal failure in childhood (reviewed by M. A. Karmali, "Infection by Verocytotoxin-producing *Escherichia coli,*" Clin. Microbiol. Rev., 2: 15–38 [1989]). Currently, blood transfusion and dialysis are the only therapies for HUS.

TTP shares similar histopathologic findings with HUS, but usually results in multiorgan microvascular thrombosis. Neurological signs and fever are more prominent in TTP, compared with HUS. Generally occurring in adults, TTP is characterized by microangiopathic hemolytic anemia, profound thrombocytopenia, fluctuating neurologic signs, fever and mild azotemia (H. C. Kwaan, "Clinicopathological features of thrombotic thrombocytopenic purpura," Semin. Hematol., 24: 71–81 [1987]; and S. J. Machin, "Clinical annotation: Thrombotic thrombocytopenic purpura," Br. J. Hematol., 56: 191–197 [1984]). Patients often die from microthrombi in the brain. In one review of 271 cases, a rapidly progressive course was noted, with 75% of patients dying within 90 days (E. L. Amorosi and J. E. Ultmann, "Thrombotic thrombocytopenic purpura: Report of 16 cases and review of the literature," Med., 45:139–159 (1966).

Other diseases associated with *E. coli* O157:H7 infection include hemorrhagic cystitis and balantitis (W. R. Grandsen et al., "Hemorrhagic cystitis and balantitis associated with verotoxin-producing *Escherichia coli* O157:H7," Lancet ii: 150 [1985]), convulsions, sepsis with other organisms and anemia (P. C. Rowe et al., "Hemolytic anemia after childhood *Escherichia coli* O157:H7 infection: Are females at increased risk?" Epidemiol. Infect., 106: 523–530 [1991]).

While the pathogenic mechanism of *E. coli* O157:H7 infection is incompletely understood, it is believed that ingested organisms adhere to and colonize the intestinal mucosa, where toxins are released which cause endothelial cell damage and bloody diarrhea. It is also postulated that hemorrhagic colitis progresses to HUS when verotoxins enter the bloodstream, damaging the endothelial cells of the microvasculature and triggering a cascade of events resulting in thrombus deposition in small vessels. These microthrombi occlude the microcapillaries of the kidneys (particularly in the glomeruli) and other organs, resulting in their failure (J. J. Byrnes and J. L. Moake, "TTP and HUS syndrome: Evolving concepts of pathogenesis and therapy," Clin. Hematol., 15: 413–442 [1986]; and T. G. Cleary, "Cytotoxin-producing *Escherichia coli* and the hemolytic uremic syndrome," Pediatr. Clin. North Am., 35: 485–501 [1988]). Verotoxins entering the bloodstream may also result in direct kidney cytotoxicity.

The role of verotoxins in the pathogenesis of *E. coli* O157:H7 infections has been further studied in animal models. Infection or toxin challenge of laboratory animals do not produce all the pathologies and symptoms of hemorrhagic colitis, HUS, and TTP which occur in humans. Glomerular damage is noticeably absent. Nonetheless, experiments using animal models implicate verotoxins as the direct cause of hemorrhagic colitis, microvascular damage leading to the failure of kidneys and other organs and CNS neuropathies.

In terms of treatment and prognosis, by the time symptoms are serious enough to attract medical attention, it is likely that verotoxins are already entering the systemic circulation or will do so shortly thereafter. Although antimicrobials may help to prevent pathology resulting from the action of toxin on the bowel lumen. However, by the time symptoms of HUS have developed, the patient has ceased shedding organisms. Thus, antimicrobial treatment during HUS disease is of less value, and often contraindicated, due to the increased risk of complications associated with administration of antimicrobials to patients susceptible to development of HUS.

III. Salmonella as a Pathogenic Organism

Worldwide, Salmonella have been isolated from humans and almost all other animal species. However, some serotypes are essentially species specific. For example, the only known natural reservoir of *S. typhi* is the human population. The same is essentially true for *S. paratyphi* types A, B, and C. Although these Salmonella are the most widely known, other of the various serotypes of Salmonella are well-documented causes of enteric and systemic disease. Many of these serotypes are associated with various wild, domestic and feral animals. For example, Salmonella infection in poultry is a serious source of food spoilage, and causes food poisoning in as many as four million people per year in the United States (Black, at p. 758).

Salmonella are associated with a wide range of infection and disease, ranging from mild, self-limiting gastroenteritis to life-threatening typhoid fever. The most common form of Salmonella disease is self-limiting gastroenteritis, with fever that lasts less than two days, and diarrhea that lasts less then one week. Typhoid, an enteric fever that is among the best-studied, is characterized by fever, headache, diarrhea, and abdominal pain. Typhoid is also sometimes associated with respiratory, hepatic, splenic, and/or neurologic damage. Other diseases associated with Salmonella include bacteremia,, meningitis, respiratory disease, cardiac disease, osteomyelitis, and local infections. Salmonella infections are particularly dangerous in patients such as the very young, the very old or immunocompromised individuals (e.g., AIDS patients).

Of the numerous Salmonella serotypes, *S. typhimurium* is most frequently isolated serotype in the United States (See e.g., L. D. Gray, "Escherichia, Salmonella, Shigella, and Yersinia," in P. Murray et al. (eds), *Manual of Clinical Microbiology*, 6th edition, ASM Press, Washington, D.C., pp. 450–456 [1995]). The nomenclature and classification of the Salmonella have changed many times over the years, and remain unsettled. For example, members of the genus Salmonella and the former genus Arizona are so closely related that they are presently considered to be one species (Salmonella). There is general consensus that there are seven distinct subgroups of Salmonella, with each group exhibiting its own phenotypic characteristics, and historical nomenclature. Most clinical isolates of Salmonella belong in group I. The members of these subgroups are serotyped according to somatic (O), surface (Vi), phase 1 flagellar and phase 2 flagellar (H) antigens. For example Salmonella subgroup 1 (*S. choleraesuis*) serotype 1,4,5,12:i:1,2, may be referred to as "Salmonella subgroup 1, serotype typhimurium, " or "Salmonella, serotype typhimurium," or "*S. typhimurium.*" The last, simple version has been in common use for many years. Indeed, the CDC has indicated its acceptance of this type of nomenclature, as being widely accepted, practical, and clinically informative (See, Gray at p. 453).

IV. Microbiological Analysis of Water and Food

As discussed above, water and food present significant risks to the public in terms of transmission of infectious disease. However, methods to directly detect and identify pathogens in food and water has proven to be problematic. Problems associated with recovery of pathogens from water and food led to the development of methods to detect and enumerate "indicators" of fecal contamination. These organisms serve to indicate whether a given water supply or food source is contaminated with fecal material, without actually testing for the presence of pathogens. This contamination is viewed as predictive of the potential presence of enteric pathogens (i.e., without the presence of fecal material, the chances of these pathogens being present is usually remote). However, a number of issues remain to be resolved, not the least of which is the significance of the presence of indicator organisms in water supplies.

Historically, "coliforms" have served as the indicator bacteria for fecal contamination in United States water supplies and food production. However, term "coliform" encompasses four genera (Escherichia, Citrobacter, Enterobacter, and Klebsiella); many of these species are commonly found in the environment in the absence of fecal contamination. Although all of these genera may be recovered from domestic sewage in large numbers, only *E. coli* is consistently and exclusively found in feces (see e.g., A. P. Dufour, "*E. coli:* the fecal coliform, in A. W. Hoadley and B. J. Dutka, *Bacterial Indicators/Health Hazards Associated with Water,* [ASTM, Philadelphia, 1976], p. 48). Thus, coliform detections methods are not specific for the determination of whether a water supply or food has been contaminated with fecal matter. Nonetheless, regulations based on detection and enumeration of "total coliforms" have been in effect in the United States since 1914 (i.e., the Treasury Department Standards of 1914; subsequent standards have been promulgated by the U.S. Public Health Service, and presently, by the U.S. Environmental Protection Agency [EPA]).

Recognition of the fact that most of the organisms included in the designation "total coliforms" are not of fecal origin, led to the development of tests to detect "fecal coliforms," for a subgroup of thermotolerant organisms included within the total coliforms. However, this designation is also not specific, as it includes *E. coli,* as well as various Klebsiella strains. Despite the fact that although there are substantial extra-fecal sources of Klebsiella, and this organism is infrequently found in human feces, the use of the "fecal coliform" designation and tests to identify these organisms remain routine (reviewed by V. J. Cabelli, "Health Effects Criteria for Marine Recreational Waters," EPA-600/1-80-031, [August, 1983], pp.1–12).

Of potential concern in the monitoring of water and food is the observation that *E. coli* O157:H7 has an optimum growth temperature that is in the range of nonfecal coliforms (e.g., *Klebsiella pneumoniae* and *Enterobacter aerogenes*), rather than the fecal coliforms (E. V. Raghubeer and J. R.

Matches, "Temperature range for growth of *Escherichia coli* serotype 0157:H7 and selected coliforms in *E. coli* medium," J. Clin. Microbiol., 28:803–805 [1990]; and M. P. Doyle and J. L. Schoeni, "Survival and growth characteristics of *Escherichia coli* associated with hemorrhagic colitis," Appl. Environ. Microbiol., 48:855–856 [1984]). Thus, routine screening for fecal coliforms by standard procedures utilizing incubation at 44.5° C. would be likely to exclude *E. coli* 0157:H7.

Furthermore, the correlation between coliform densities in water and the incidence of waterborne disease originally postulated by Kehr and Butterfield in 1943 (R. W. Kehr and C. T. Butterfield, "Notes on the relationship between coliforms and enteric pathogens," Public Health Repts. 58:589–596 [1943]) have not been supported by experimental tests (Batik et al., "Routine monitoring and waterborne disease outbreaks," J. Environ. Health 45:227–230 [1984]). Quite simply, there has been no direct evidence presented that the level of coliform contamination correlates well with waterborne disease outbreaks (see Pipes, p. 434–435). Nonetheless, due to the lack of better methods, the detection of coliforms as indicator bacteria continues into the present.

Coliform detection may be accomplished by various methods, including multiple tube fermentation (i.e., most probable number or "MPN" determinations), membrane filtration, the "presence-absence" test, and various rapid enzyme (e.g., the MUG test) and immunoassay methods. Important considerations with these methods include the large time, equipment and personnel commitment necessary to conduct and interpret these tests.

Most Probable Number (MPN). The MPN method is a labor, time and supply intensive method, which involves three distinct stages of specimen processing (the presumptive (with lauryl tryptose broth), completed (with brilliant green lactose bile broth) and confirmed tests (with LES Endo or EMB). The MPN method requires 3–4 days in order to produce confirmatory results, and statistical analysis to quantitate the organisms present.

This procedure has been developed to separate organisms within the coliform group into "total" and "fecal" coliforms. Prior enrichment of organisms in a presumptive test medium is required for optimum recovery of fecal coliforms. These methods are used as confirmatory tests conducted with various selective media and elevated incubation temperatures (e.g., 44.5° C.). Thus, there is also a significant time and labor commitment associated with these methods.

Membrane Filtration. In membrane filtration, a known volume of water sample is passed through a membrane filter which is then placed on growth media (e.g., M-Endo or LES-Endo), and incubated overnight. All colonies with characteristics common to coliforms are considered to be members of the coliform group. An advantage of membrane filtration is that preliminary results are usually available in 24 hours. However, verification of colony identification is recommended, usually requiring additional days in order to conduct the needed biochemical tests.

Membrane Filtration Method Modifications. A seven hour fecal coliform test similar to the membrane filtration process has also been described. In this technique, the water sample is filtered and the filter placed on M-7 FC agar and incubated at 41.5° C. (American Public Health Association-American Water Works Association-Water Pollution Control Federation, *Standard Methods for the Examination of Water and Wastewater*, 16th ed., [APHA, Washington, D.C.], 1985; hereinafter, "Standard Methods"). Yellow colonies representing fecal coliforms are enumerated after seven hours of incubation. However, different growth rates of colonies necessitate a compromise between sensitivity of detection and enumeration. That is to say, because different organisms grow at different rates, some organisms will not have had sufficient time to produce visible colonies on the medium by the time enumeration is conducted. However, the value of this test is perhaps questionable, in view of its deletion from the most recent edition of Standard Methods.

Another method developed by Reasoner, in conjunction with Geldreich (D. J. Reasoner and E. E. Geldreich, "Rapid detection of water-borne fecal coliforms by $^{14}CO_2$ release," in A. N. Sharpe and D. S. Clark, (eds.) *Mechanizing Microbiology*, [Charles C. Thomas Publishers, 1978], pp. 120–139) involves concentration of bacteria on a membrane filter which is then placed in M-FC broth which contains radiolabelled $^{14}C$-mannitol. The tubes are incubated for 2 hours at 35° C., followed by 2.5 hours at 44.50. Release of $^{14}CO_2$ due to microbial metabolism is then assayed by liquid scintillation spectrometry. Major problems with these methods involve the use of radioactivity and the attendant disposal and handling concerns, as well as the need for specialized and expensive instruments.

An alternate radioactive test was developed by Dange el al. (V. Dange et al., "One hour portable test for drinking waters," Water Res., 22:133–137 [1988]). This method is based on the correlation of $^{32}P$ uptake by organisms present in a water sample incubated in a synthetic medium. Thus, these methods require highly trained laboratory personnel and are not suitable for use in many labs.

Presence-Absence Test. The presence-absence test to detect the presence of coliforms involves the inoculation of broth with 100 ml samples of water, followed by incubation at 25° C. for 24–48 hours. If acid and gas is produced in the medium, the test is positive for the presence of coliforms (see e.g., Standard Methods, at p. 882–884). No enumeration of organisms is attempted, nor are any identification methods utilized. Thus, the information garnered from this method is very limited.

Fluorometric and Enzymatic Tests. Detection methods for coliforms with fluorometric tests and numerous variations on the basic technology have also been developed. Other substrate-based methods include the use of such compounds as ortho-nitrophenyl-β-D-galactopyranoside (ONPG), 5-bromo-4-chloro-3-indolyl-β-D-glucuronide (X-GLUC) (see e.g., E.W. Frampton et al., "Evaluation of the β-glucuronidase substrate 5-bromo-4-chloro-3-indolyl-β-D-glucuronide (X-GLUC) in a 24-hour direct plating method for *Escherichia coli*," J. Food Protect., 51:402–404 [May 1988]; and L. Restaino et al., "Use of the chromogenic substrate 5-bromo-4-chloro-3-indolyl-β-D-glucuronide (X-GLUC) for enumerating *Escherichia coil* in 24 H from ground beef," J. Food Protect., 53:508–510 [1990]);, and 4-methylumbelliferyl-β-D-glucuronide (MUG). These methods utilize fluorogenic or chromogenic substrates to detect coliform metabolism, as opposed to direct detection and enumeration of organisms. Thus, the only data available from these test methods relate to the presence or absence of organisms which possess the necessary enzymatic machinery to produce the detectable color compounds from a given substrate.

The MUG test is also problematic in that many clinically important *E. coli* strains are negative (see e.g., E. W. Frampton and L. Restaino, "Methods for *Escherichia coli* identification in food, water and clinical samples based on beta-glucuronidase detection," J. Appl. Bacteriol., 74:223–233 [1993]). Indeed, there is a significant proportion of β-glucuronidase-negative *E. coli* (see e.g., G. W. Chang et al., "Proportion of β-D-glucuronidase-negative *Escheri*-

*chia coli* in human fecal samples," Appl. Environ. Microbiol., 55:335–339 [1989]). Furthermore, species within other genera such as Staphylococcus, Streptococcus, Clostridium, and the anaerobic corynebacteria also produce β-glucuronidase (Frampton and Restaino, p. 223). Thus, not only is the test not highly sensitive, it is not specific. These reports raise serious questions regarding the reliability of these testing methods.

Bacteriophages. In addition to culture and enzymatic detection methods, bacteriophages have also been used with some limited success as indicators of fecal contamination (R. S. Wensel et al., "Evaluation of coliphage detection as a rapid indicator of water quality," Appl. Environ. Microbiol., 43:430–434 [1982]; Y. Kott et al., "Bacteriophages as bacterial viral pollution indicators," Water Res., 8:165–171 [1982]; and A. H. Havelaar et al., "Factors effecting the enumeration of coliphages in sewage and sewage-polluted waters," Antonie van Leeuwenhoek 49:387–397 [1983]).

However, the detection limits provided by these methods are no better than those obtained with standard methods for water quality determinations based on coliform analysis. Thus, these methods do not provide a significant advantage over the traditional methods of water analysis. Likewise, the presence of coliforms in a particular water or food sample does not necessarily correlate well with the incidence of disease. Even the enumeration of "fecal coliforms" is less than optimal, as some organisms such as Klebsiella are capable of producing positive test results. Such observations led to the development of alternative indicator organisms, including tests specific for *E. coli*, fecal streptococci (e.g., enterococci), Klebsiella, *Clostridium perfringens, Pseudomonas aeriginosa,* Bifidobacterium, Bacteroides, *Aeromonas hydrophila, V. parahaemolyticus,* and *C. albicans,* as well as other organisms commonly excreted in large numbers by healthy mammals. What remains to be developed is a method for the detection and enumeration of pathogens commonly associated with water and food-borne diarrheal illness.

V. Diagnosis of Enteric Disease/Infection

The diagnosis of infectious disease has traditionally relied upon microbiological culture methods to identify the causative organism and determine the appropriate antimicrobial treatment. This has remained so despite recent advances in molecular and immunological diagnostics. While the development of rapid and automated methods has served to increase the efficiency of microbiological analysis, traditional methods remain critical for definitive diagnosis of infections (Baron & Finegold, p. 253). As discussed above, isolation and identification of pathogens in environmental samples, food, and water present additional considerations. For example, the methods available for detecting *E. coli* 0157:H7 in food are extremely time-consuming, or are not highly specific (N. V. Padhye and M. P. Doyle, "Rapid procedure for detecting enterohemorrhagic *Escherichia coli* 0157:H7 in food," Appl. Environ. Microbiol., 57:2693–2698 [1991]). Nonetheless, clinical, as well as food, water, and environmental samples must be analyzed for the presence of pathogens.

After proper specimen collection and transport, the laboratory professional must determine which of a multitude of culture media are most appropriate to use with the culture at hand. It is important to consider the type of specimen (e.g, urine, blood, sputum, etc.), and the most commonly isolated organisms associated with disease or infection at the site of specimen collection. The time and cost necessary to achieve a final diagnosis also must be borne in mind. For gastrointestinal samples (e.g, fecal samples, rectal swabs, colonoscopy samples, etc.) the presence of a large complement of commensal organisms in the gastrointestinal tract necessitates the use of media and procedures to optimize growth of pathogenic organisms, while differentiating them from the normal flora. Numerous organisms are included among the normal flora of healthy individuals, including *S. epidermidis, S. aureus,* viridans streptococci, enterococci, *S. pyogenes* and other streptococci, peptostreptococci, lactobacilli, corynebacteria, mycobacteria, clostridia, actinomycetes, various members of the Enterobacteriaceae, *P. aeruginosa, Alcaligenes faecalis,* Flavobacterium spp., Bacteroides spp., Fusobacterium spp., Eubacterium spp., Propionibacterium spp., Bifidobacterium spp., yeasts, filamentous fungi, and various protozoans (e.g., *Entamoeba coli, Endolimax nana, Iodamoeba butschlii, Trichomonas hominis,* and *Chilomaslix mesnili*) (see e.g., H. D. Isenberg and R. F. D'Amato, "Indigenous and Pathogenic Microorganisms of Humans," in P. Murray et al. (eds), *Manual of Clinical Microbiology,* 6th edition, ASM Press, Washington, D.C., [1995]), p.9). Enrichment techniques are often required for successful isolation of Salmonella, Shigella and Vibrio. These enrichment media work on the principle that normal fecal flora are maintained in a prolonged lag phase by inhibitory compounds present in the growth media, while the organism enriched for (e.g., Salmonella and Shigella) are far less inhibited, enter the log phase of growth and are more readily recovered (See e.g., E. W. Koneman et al., *Color Atlas and Textbook of Diagnostic Microbiology,* 4th ed., J. B. Lippincott Co., Philadelphia [1992], p. 119).

Traditionally, it has been recommended that laboratories routinely examine specimens for the presence of Salmonella, Shigella, Campylobacter, Aeromonas, and Plesiomonas, as well as predominating numbers of *S. aureus,* yeasts, Pseudomonas spp., Yersinia spp., and some Vibrio spp. from cases of gastrointestinal disease (,See e.g., A. Grasmick, "Processing and Interpretation of Bacterial Fecal Cultures," in "Section I. Aerobic Bacteriology," in H. Isenberg (ed.), *Clinical Microbiology Procedures Handbook,* American Society for Microbiology, Washington, D.C., [1994], p. 1.10.5; and Baron and Finegold, at 61, 247–251). Each laboratory must assess the patient history, the patient population associated with the laboratory or hospital, the geographic location of the facility, and hospital size in order to choose the selective and differential media that will be routinely used to culture fecal samples. Routine cultures for isolation of enteric organisms from clinical specimens usually include a blood agar plate (for aerobic incubation), at least one differential medium (e.g., MacConkey and EMB agars), at least one moderately selective medium (e.g., Hektoen-enteric (HE agar), Xylose-lysine ]deoxycholate (XLD agar), Salmonella-Shigella (SS agar), desoxycholate, desoxycholate-citrate, and desoxycholate-lactose agars), and at least one enrichment broth (e.g., tetrathionate broth, selenite F broth, selenite cystine broth, Hajna broth, and Gram-negative broth (GN)). Media for selective isolation and enrichment of Campylobacter (e.g., Skirrow's, Blaser's, Butzler's, or Preston's formulae, and Campy-THIO agars) and special incubation conditions (i.e., a microaerophilic atmosphere and 42° C.) are also included, as are media for Aeromonas (a blood agar plate with 10 µg/ml ampicillin), Plesiomonas (inositol-brilliant-green bile-salts agar), and Yersinia (cefsulodin-irgasan-novobiocin agar [CIN]), and Vibrio (thiosulfate citrate bile salts agar [TCBS], and peptone broth for enrichment). Additional plates sometimes include media selective for *C. difficile* (cycloserine-cefoxitin-fructose-egg yolk agar [CCFA]). In the investigation of an outbreak, at least one highly selective medium (e.g., brilliant green, and bismuth sulfite agars), as well as any other media and incubation conditions indicated by the type of disease (e.g., special anaerobic media and anaerobic incubation, media for isolation of mycobacteria, or media for isolation of *Helicobacter pylori*) are added to the battery of media inoculated. Thus, for each sample, numerous plated and broth media are inoculated for primary isolation of enteric organisms. Many of the same media are routinely used for isolation and identification of pathogenic organisms from food, dairy and water samples, especially in outbreak situations.

Selective Media for *E. coli* and Salmonella Species

In 1993, the CDC recommended that all laboratories routinely culture for *E. coli* 0157:H7 from all patients presenting with diarrhea (See, Gray, at p. 452). Fecal samples should be cultured within 7 days of the onset of intestinal illness in adults and within 30 days of onset of intestinal illness in children (See, Gray at p. 452). More emphatically, fecal samples should be collected from any patient who reports having bloody diarrhea, and tested for *E. coli* 0157:H7.

MacConkey-sorbitol agar (SMAC) is the most commonly used medium for isolation of *E. coli* 0157:H7 and provides a preliminary characterization of *E. coli* isolates suspected of being *E. coli* 0157:H7 (S. B. March and S. Ratnam, "Sorbitol-MacConkey medium for detection of *Escherichia coli* 0157:H7 associated with hemorrhagic colitis," J. Clin. Microbiol., 23:869–872 [1986]). *E. coli* colonies that do not ferment sorbitol (i.e., non-colored colonies) may be further characterized by serotyping and/or testing for verotoxin production. Nearly all *E. coli* 0157:H7 isolates do not ferment sorbitol, whereas most non-pathogenic *E. coli* isolates ferment this substrate.

Unfortunately, SMAC has a very major drawback in that it is not highly specific for detecting *E. coli* 0157:H7. One problem is that other sorbitol-negative *E. coli* will also be detected as false positives on this medium. Indeed, as many as 20% of clinical isolates of *E. coli* may be sorbitol-negative (NCASM Winter Newsletter, [1994] p. 4). In addition, many other species such as Aeromonas, *Budvicia aquatica, Buttiauxella agrestis, Cedecea davisae, Enterobacter agglomerans* biogroups 2, 3, 4, and 6, *E. laylorae, Erwinia carotovora, Escherichia blattae, E. alkalescens-dispar, E. fergusonii, E. hermanii, E. vulneris, Ewingella americana, Klebsiella pneumoniae* ss. *rhinoscleromatis, Kluyvera cryocrescens, Lecleria adecarboxylata, Leminorella grimontii, L. richardii, Morganella morganli, Obesumbacterium proteus* biogroup 2, *Plesiomonas shigelloides, Pragia fontium, Proteus mirabills, P. myxofaciens, P. vulgaris, Providencia alcalifaciens, P. heimbachae, P. rettgeri, P. rustiganni, P. stuartii, Serratia entomophila, S. plymuthica, Shigella boydii, S. flexneri, S. sonnel, Xenorhabdus nematophilus, Yersinia pestis, Y pseudotuberculosis, Y ruckeri,* and *Yokenella regensburgei* also grow as non-colored colonies on SMAC.

Furthermore, some rare isolates of *E. coil* 01 57:H7 have been reported as being sorbitol-positive (See e.g., P. M. Frantamico et al., "Virulence of an *Escherichia coli* 0157:H7 sorbitol-positive mutant," Appl. Environ. Microbiol., 59:4245–4252). Thus, these sorbitol-positive isolates would be assumed to be normal fecal flora, and not be considered for further identification and testing upon their isolation on SMAC and it is likely that the patient's disease would be undiagnosed.

An ideal medium would also detect other *E. coli* serotypes, in addition to *E. coli* 0157:H7, as other serotypes have been shown to produce verotoxins or other shiga-like toxins, and have also been associated with clinical disease (See Table 5). However, these other serotypes are not differentiated on SMAC because they are sorbitol-positive (see e.g., M. Ritchie et al., "Comparison of a direct fecal shiga-like toxin assay and sorbitol MacConkey agar culture for laboratory diagnosis of enterohemorrhagic Escherichia coli infection," J. Clin. Microbiol., 30:461–464 [1992]).

In addition to their characteristic inability to ferment sorbitol, most *E. coli* 01 57:H7 isolates do not produce β-glucuronidase, and cannot cleave glucuronidase substrates such as 4-methylumbelliferyl-β-D-glucuronide (MUG). This property also serves as a means to help differentiate many non-pathogenic *E. coli* isolates from non-0157:H7, as most of the non-pathogenic isolates are capable of cleaving MUG to produce a fluorescent product that is visible under UV light (i.e., these isolates are MUG-positive, while *E. coli* 0157:H7 is MUG-negative; J. S. Thompson et al., "Rapid biochemical test to identify verocytotoxin-positive strains of *Escherichia coli* serotype 0157," J. Clin. Microbiol., 28:2165–2168 [1990]). However, the fluorescent product in this test diffuses out of the colonies, obscuring the actual colonial source of the enzyme.

Some researchers have investigated the addition of chromogenic glucuronidase substrates such as 5-bromo-4-chloro-3-indoxyl-β-glucuronide (X-GLUC) to SMAC (A. J. G. Okrend et al., "Use of 5-bromo-4-chloro-3-indoxyl-β-glucuronide in SMAC to aid in the isolation of *Escherichia coli* 0157:H7 from ground beef," J. Food Protect., 53:941–943 [1990]; and F. Nimoorand and C. Lord, J. Rapid Meth. Automation Microbiol., 3:85–96 [1994]). However, these media only help differentiate β-glucuronidase-positive, sorbitol-negative *E. coli* isolates. It does not differentiate other glucuronidase-negative, sorbitol-negative *E. coli* isolates, or any of the other species that grow as non-colored colonies on SMAC discussed previously. Thus, additional work is necessary to differentiate between *E. coli* 0157:H7 and other species which grow as non-colored colonies on this medium.

In yet another SMAC-based medium for *E. coli* 0157:H7, rhamnose and cefixime are incorporated in SMAC. This medium has been reported to be somewhat beneficial, as cefixime inhibits Proteus, and rhamnose is fermented by most non-sorbitol fermenting *E. coli* serogroups other than 0157:H7 (P. A. Chapman et al., "An improved selective medium for the isolation of *Escherichia coli* 0 157," J. Med. Microbiol., 35:107–110 [1991]). This medium has a disadvantage in that although the false positive rate is lower compared with regular SMAC, numerous colonies are still isolated that are not *E. coli* 0157:H7. Furthermore, many *E. coil* 0157:H7 isolates are rhamnose-positive (S. L. Abbott et al., "*Escherichia coli* 0157:H7 generates a unique biochemical profile on MicroScan conventional gram-negative identification panels," J. Clin. Microbiol., 32:823–824 [1994]) and would not be detected on this medium.

Still another variation incorporates tellurite and cefixime in SMAC (P. M. Zadik et al., "Use of tellurite for the selection of verocytotoxigenic *Escherichia coli* 0157," J. Med. Microbiol., 39:155–158 [1993]). However, even the tellurite-containing medium had a high rate of false positives ("[t]he suppression of non-0157 *E. coli* on TC-SMAC uncovered a large number of NSF [non sorbitol fermenting] colonies (206 among the 391 specimens) that required screening by latex agglutination for 0157."

Several non-MacConkey sorbitol-containing media have been developed for isolation and preliminary identification of *E. coil* 0157:H7. One medium incorporates tryptone, sorbitol, sodium chloride, bile salts, bromcresol purple, and MUG (R. A. Szabo et al., "Method to isolate *Escherichia coli* 0157:H7 from food," J. Food Protect., 49:768–772 [1986]). Organisms are grown overnight at 44.5° C. on membrane filters placed on top of the agar medium. This method also depends upon the non-utilization of sorbitol to differentiate between *E. coil* 0157:H7 and other serotypes. On this medium, *E. coli* 0157:H7 is reported as being sorbitol-negative, MUG-negative, and indole-positive. Non-0157:H7 *E. coil* are sorbitol-positive, MUG-positive, and appear to be indole-negative, due to utilization of sorbitol, which is preferentially metabolized over tryptophan (in the tryptone). However, upon prolonged incubation, these colonies can appear to be indole-positive. As this method uses incubation at an elevated temperature, it is possible that many isolates of *E. coil* 0157:H7 would not be detected (E. V. Raghubeer and J. R. Matches, "Temperature range for growth of *Escherichia coli* serotype 0157:H7 and selected coliforms in *E. coil* medium," J. Clin. Microbiol., 28:803–805 [1990]; and M. P. Doyle and J. L. Schoeni, "Survival and growth characteristics of *Escherichia coli* associated with hemorrhagic colitis," Appl. Environ. Microbiol., 48:855–856 [1984]). In addition, some types of membrane filters appear to inhibit some *E. coli* 0157:H7 isolates.

Another modified sorbitol-containing medium has also been described, which incorporates antiserum directed against H7 (J. J. Farmer and B. R. Davis, "H7 antiserum-sorbitol fermentation medium: A single tube screening medium for detecting *Escherichia coli* 0157:H7 associated with hemorrhagic colitis," J. Clin. Microbiol., 22:620–625 [1985]). This medium is highly selective for *E. coli* 0157:H7, as only about 10% of other *E. coli* strains have the H7 antigen and about 95% of the non-01 57:H7 *E. coli* strains ferment sorbitol. However, it requires production and ready supply of anti-H7 antiserum, special handling to incorporate the antiserum into the medium, and would likely to be expensive if made commercially available.

Still another approach utilizes enrichment in EC broth with novobiocin for 24 hours (for optimal results), followed by isolation on several media, (e.g., SMAC, phenol red sorbitol agar with MUG, and EMB) (A. J. G. Okrend et al., "A screening method for the isolation of *Escherichia coli* 0157:H7 from ground beef," J. Food Protect., 53:249–252 [1990]). This method requires a minimum of two days and multiple plates of media, in order to obtain an identification. It is slow, labor-intensive and also suffers from lack of specificity (as described previously for the other methods).

Other methods, such as immunoassays have been developed to screen samples such as food for the presence of *E. coli* 0157:H7 (see e.g., M. S. Kim and M. P. Doyle, "Dipstick immunoassay to detect enterohemorrhagic *Escherichia coli* 0157:H7 in retail ground beef," Appl. Environ. Microbiol., 58:1764–1767 [1992]). However, these methods are time-consuming, require the production of monoclonal antibodies and the optimization of such immunoassay systems as ELISA's. In addition, immunological methods are not likely to detect all verotoxins with equal efficiency and may not detect some at all (Gannon et al., "Rapid and sensitive method for detection of Shiga-like toxin-producing *Escherichia coli* in ground beef using the polymerase chain reaction," Appl. Environ. Microbiol., 58:3809–3815 [1992]).

Molecular methods, such as the polymerase chain reaction (PCR) have been used to differentiate between types or variants of verotoxin genes (M. P. Jackson, "Detection of Shiga toxin-producing *Shigella dysenteriae* type 1 and *Escherichia coli* using the polymerase chain reaction with incorporation of digoxigenin- 11-dUTP," J. Clin. Microbiol., 29:1910–1914 [1991]; W. M. Johnson et al., "Amplification by the polymerase chain reaction of a specific target sequence in the coding for *Escherichia coli* verotoxin (VTe) variant," FEMS Microbiol. Lett., 84:227–230 [1991]; and H. Karch and T. Meyers, "Single primer pair for amplifying segments of distinct Shiga-like toxin genes by polymerase chain reaction," J. Clin. Microbiol., 287:2751–2757 [1989]). There are a few reports of development of PCR methods to detect verotoxin gene sequences in samples such as ground beef (see e.g., Gannon el al.). However, these molecular methods require equipment (e.g., thermal cyclers, etc.), and expertise that this not commonly available in most microbiology laboratories.

Some methods, such as cell culture-based verocytotoxin assays have been developed to detect the presence of toxin, rather than the presence of organisms. However, these cell culture methods require the maintenance of cell cultures, a burden that cannot be met by many laboratories, especially food, water, and environmental laboratories. Indeed, cell cultures are often maintained by virology laboratories, rather than microbiology laboratories (i.e.,traditional bacteriology laboratories). Many laboratories do not have the specialized equipment and expertise necessary to maintain cell cultures. Thus, these methods are not readily adaptable to field situations nor other settings where minimal laboratory capabilities are common.

Thus, better methods for isolation and identification of *E. coli* 0157:H7 are needed. Indeed, after completing their recent survey of methodologies, Nimoorand et al., concluded that "[a] better enrichment medium, as well as improved selective plating and confirmation techniques, are needed to enhance the selective growth of *E. coli* 0157:H7 and provide lower detection levels," F. Nimoorand and C. Lord, J. Rapid Meth. Automation Microbiol., 3:85–96 [1994]).

Additional media of more general use in isolation and enumeration of *E. coli* are disclosed in such patents as U.S. Pat. No. 3,870,601 to Warren et al. (herein incorporated by reference), which describes a culture medium for differentiation of Enterobacteriaceae based on a combination of a chromogenic β-galactosidase substrate, along with substrates for decarboxylase, deaminase, and/or urease, a hydrogen sulfide detection system, and/or a carbohydrate fermentation system. Another medium is disclosed in U.S. Pat. No. 4,070,247 to Burt (herein incorporated by reference), which reduces the incidence of false negative lactose fermentation results, and permitting differentiation between lac inducible and lac constitutive bacteria due to incorporation of isopropyl-β-D-thiogalactopyranoside in the medium. Another medium is disclosed in U.S. Pat. No. 5,210,022 to Roth et al., which utilizes chromogenic β-galactosidase substrate and chromogenic β-glucuronidase substrates to differentiate between coliforms (species other than *E. coli*) and *E. coli*. Yet another medium is disclosed in PCT Appln. No. PCT/FR93/00988 (WO 94/08043) to Rambach (herein incorporated by reference), which utilizes a chromogenic glucuronidase substrate to isolate and enumerate *E. coli*.

Various media and methods have also been developed, with varying degrees of success, for the isolation and identification of Salmonella species. This is exemplified by the numerous media formulations listed in Section V above, which are commonly used in clinical microbiology laboratories to selectively enrich, isolate and differentiate Salmonella.

In a very recent study (H. Dusch and M. Altwegg, "Evaluation of five new plating media for isolation of Salmonella species," J. Clin. Microbiol., 33:802–804 [1995]), HE (BBL) was compared with Rambach agar (Ra; E. Merck, Darmstadt, Germany), SM-ID medium (SM; bioMériéux), XLT4 (xylose-lysine-Tergitol®-4 agar; Difco); brilliant green-glycerol-lactose agar (NGBL; not commercially available; D. M. Poisson, "Novobiocin, brilliant green, glycerol lactose agar: A new medium for the isolation of Salmonella strains," Res. Microbiol., 143:211–216 [1992]), and modified semisolid Rappaport Vassiliadis medium (MSRV; Difco). The XLT4 medium used in this study is described in U.S. Pat. No. 5,208,150, to Tate et al. (herein incorporated by reference). Rambach agar used in this study is described in Rambach, "New plate medium for facilitated differentiation of Salmonella spp. from Proteus spp. and other enteric bacteria," Appl. Environ. Microbiol., 56:303–303 [1990]; see also, U.S. Pat. Nos. 5,098,832 and 5,194,374 to Rambach).

These authors found that MSRV was the most sensitive of the media tested, and was very specific for the isolation of non-S. typhi from stool specimens. However, the semisolid nature of the medium was found to be a disadvantage and required careful handling in the laboratory. In addition, MSRV, as well as XLT4 and Ra are not suitable for use in the isolation of S. typhi and S. paratyphi type A (Dusch and Altwegg, at p. 804). Thus, these important organisms would be missed, if these media were used exclusively.

Additional media have been tested for their suitability to detect and provide a preliminary identification of Salmonella species in general, and S. typhi in particular. In one study, a lysine-mannitol-glycerol agar (LMG) was developed for isolation of Salmonella, including S. typhi (J. M. Cox, "Lysine-mannitol-glycerol agar, a medium for the isolation of Salmonella spp., including S. typhi and atypical strains," Appl. Environ. Microbiol., 59:2602–2606 [1993]). This medium combines the characteristics of XLD and mannitol-lysine-crystal violet-brilliant green agar, with the addition of glycerol to aid in the differentiation of Salmonella and Citrobacter. The medium facilitates detection of strains with atypical fermentation patterns, such as the lactose or sucrose-positive Salmonella. However, it was not suitable for the isolation of other atypical strains, such as hydrogen sulfide-negative and lysine decarboxylase-negative strains. Also, there was a high percentage of false positive Citrobacter isolates which were observed on this medium. In addition, enrichment was found to be required for optimal detection of S. typhi.

A further modification of LMG developed for isolation of Salmonella from clinical specimens incorporates sulphamandelate in lysine mannitol glycerol agar [LMGS] (K. R. Stallard and J. M. Cox, "Lysine mannitol glycerol agar (LMG) and LMG with sulfphamandelate for isolation of Salmonella spp. from clinical specimens," Lett. Appl. Microbiol., 19:83–87 [1994]). In a comparison of this medium with LMG, it was found to be superior, in terms of sensitivity of detection and selectivity for Salmonella. Although this medium performed better than LMG, a high percentage of false positive Citrobacter isolates was observed. In addition, this medium was only used in conjunction with enrichment methods. Thus, its suitability as a primary isolation medium without a pre-enrichment step is unknown.

In summary, despite a long-standing recognized need and the efforts of many pepole to develop better enrichment and isolation media for E. coli and Salmonella species in general, and E. coli 0157:H7 in particular, all of the media developed to date have important drawbacks and limitations. Indeed, there remains a critical need for media suitable for use in food, water, veterinary, and clinical testing, which would provide rapid, specific and reliable results (See e.g., N. V. Padhye and M. P. Doyle, "Escherichia coli 0157:H7: Epidemiology, pathogenesis, and methods for detection in food," J. Food Protect., 55:555–565 [1992]).

SUMMARY OF THE INVENTION

The present invention describes test media and methods for the growth, isolation, and presumptive identification of bacterial organisms. The present invention contemplates compounds and formulations, as well as methods particularly suited for the detection and presumptive identification of organisms most often associated with gastrointestinal infections. It is contemplated that the present invention will be used for growth, isolation, and identification of such enteric pathogens as E. coli and Salmonella. The present invention also provides a means to differentiate between E. coli 0157:H7 and other verotoxin-producing E. coli serotypes, as well as differentiation between pathogenic and non-pathogen E. coli isolates. Importantly, the present invention also provides a means for growth, isolation and preliminary identification of Salmonella, including S. typhi and S. paratyphi, as well as other serogroups, including S. enteritidis and S. arizonae.

One embodiment of the present invention is a medium for the growth of bacteria comprising propionic acid, one or more inhibitable chromogenic substrates, a nutrient base. In one embodiment, the nutrient base comprises one or more compounds selected from the group consisting of peptones, extracts, infusions, amino acids, vitamins, nitrogen, phosphorus, sulfur, magnesium, manganese, iron, and potassium. In a preferred embodiment, the one or more inhibitable chromogenic substrates comprising galactosidase substrates and glucuronidase substrates. In a particularly preferred embodiment, the galactosidase substrate is selected from the group comprising consisting of indoxyl-β-D-galactoside, 5-bromo-3-indolyl-,β-D-galactoside, and 5-bromo-4-chloro-3-indolyl-β-D-galactoside. In an alternative preferred embodiment, the medium further comprises one or more compounds selected from the group consisting of sorbitol, arabitol, and cellobiose.

In one embodiment, the medium is a broth. In an alternative embodiment, the medium comprises a gelling agent. Thus, the present invention contemplates various forms of the media of the present invention, ranging from broths (i.e., liquid or fluid), semi-solid (i.e., thickened or viscous liquids), to solid media (i.e., gelled media, such as the agar plates commonly used in microbiology laboratories).

In another embodiment, the present invention comprises a medium for the growth of bacteria, comprising one or more inhibitable galactosidase chromogenic substrates, one or more compounds selected from the group consisting of sorbitol, arabitol and cellobiose, and a nutrient base. In one embodiment, the nutrient base comprises one or more compounds selected from the group consisting of peptones, extracts, infusions, amino acids, vitamins, nitrogen, phosphorus, sulfur, magnesium, manganese, iron, and potassium. In a preferred embodiment, the chromogenic galactosidase substrate is selected from the group consisting of indoxyl-β-D-galactoside, 5-bromo-3-indolyl-β-D-galactoside, and 5-bromo-4-chloro-3-indolyl-β-D-galactoside. In an alternative preferred embodiment, the medium further comprises a chromogenic glucuronidase substrate. In one preferred embodiment, the chromogenic glucuronidase substrate is selected from the group comprising 6-chloro-3-indolyl-β-D-glucuronide, 5-bromo-6-chloro- 3-indolyl-β-D-glucuronide, and 5-bromo-4-chloro-3-indoxyl-β-glucuronide. In a particularly preferred embodiment, the medium further comprises propionic acid.

It is contemplated that the media of the present invention will be useful in various formats. For example, in one embodiment, the medium is a broth. In an alternative embodiment, the medium comprises a gelling agent. Thus, the present invention contemplates various forms of the media of the present invention, ranging from broths (i.e., liquid or fluid), semi-solid (i.e., thickened or viscous liquids), to solid media (i.e., gelled media, such as the agar plates commonly used in microbiology laboratories).

In another alternative embodiment, the present invention comprises a medium for the growth of bacteria comprising a nutrient base, and two or more carbon sources selected from the group comprising propionic acid, methyl-glucuronide, lactose, D-malic acid, L-galactonic acid lactone, D-galacturonic acid, itaconic acid, tricarballylic acid, α-keto-butyric acid, D-aspartic acid, glucosaminic acid, citric acid, threonine, para-hydroxyphenylacetic acid, ethanolamine, N-acetylmannosamine, and tyramine. In one embodiment, the nutrient base comprises one or more compounds selected from the group consisting of peptones, extracts, infusions, amino acids, vitamins, nitrogen, phosphorus, sulfur, magnesium, manganese, iron, and potassium. As with the other embodiments, it is contemplated that various formats of the medium will be used. In a particularly preferred embodiment, the medium further comprises one or more compounds selected from the group comprising chromogenic galactosidase substrates, glucuronidase substrates and tetrazolium dyes.

In another embodiment, the present invention comprises a method for detecting the presence of enteric bacteria in a test sample suspected of containing enteric bacteria, comprising the steps of inoculating a medium with test sample, wherein the medium comprises propionic acid and a nutrient base, and incubating the medium under conditions wherein enteric bacteria can grow. In one embodiment, the nutrient base comprises one or more compounds selected from the group consisting of peptones, extracts, infusions, amino acids, vitamins, nitrogen, phosphorus, sulfur, magnesium, manganese, iron, and potassium. In a preferred embodiment, the chromogenic substrate is inhibitable. In a particularly preferred embodiment, the inhibitable chromogenic substrate is selected from the group comprising galactosidase substrates and glucuronidase substrates. In one preferred embodiment, the chromogenic galactosidase substrate is selected from the group comprising consisting of indoxyl-β-D-galactoside, 5-bromo-3-indolyl-β-D-galactoside, and 5-bromo-4-chloro-3-indolyl-β-D-galactoside. In yet another preferred embodiment, the medium further comprises one or more compounds selected from the group consisting of sorbitol, arabitol, and cellobiose.

It is also contemplated that the medium used in the method of the present embodiment will be useful in various formats. For example, in one embodiment, the medium is a broth. In an alternative embodiment, the medium comprises a gelling agent. Thus, the present invention contemplates various forms of the media of the present invention, ranging from broths (i.e., liquid or fluid), semi-solid (i.e., thickened or viscous liquids), to solid media (i.e., gelled media, such as the agar plates commonly used in microbiology laboratories). In another preferred embodiment, the medium further comprises a tetrazolium dye. It a particularly preferred embodiment, the enteric bacteria are selected from the group consisting of verotoxin-producing or verotoxin non-producing $E.$ $coli$ and Salmonella.

In another embodiment, the present invention comprises a method for the detecting the presence of bacteria in a test sample suspected of containing bacteria comprising the steps of inoculating a medium for the growth of bacteria, wherein the medium comprises one or more inhibitable galactosidase chromogenic substrates, one or more compounds selected from the group consisting of sorbitol, arabitol and cellobiose, a nutrient base; incubating the medium under conditions wherein bacteria can grow; and examining the medium for the presence of bacteria. In one embodiment, the nutrient base comprises one or more compounds selected from the group consisting of peptones, extracts, infusions, amino acids, vitamins, nitrogen, phosphorus, sulfur, magnesium, manganese, iron, and potassium. In another preferred embodiment, the chromogenic galactosidase substrate is selected from the group consisting of indoxyl-β-D-galactoside, 5-bromo-3-indolyl-β-D-galactoside, and 5-bromo-4-chloro-3-indolyl-β-D-galactoside. In an alternative preferred embodiment, the medium further comprises one or more chromogenic glucuronidase substrate. In one preferred embodiment, the chromogenic glucuronidase substrate is selected from the group comprising 6-chloro-3-indolyl-β-D-glucuronide, 5-bromo-6-chloro-3-indolyl-β-D-glucuronide, and 5-bromo-4-chloro-3-indoxyl-β-glucuronide. In a particularly preferred embodiment, the medium further comprises propionic acid.

It is also contemplated that the medium used in this method of the present embodiment will be useful in various formats. For example, in one embodiment, the medium is a broth. In an alternative embodiment, the medium comprises a gelling agent. Thus, the present invention contemplates various forms of the media of the present invention, ranging from broths (i.e., liquid or fluid), semi-solid (i.e., thickened or viscous liquids), to solid media (i.e., gelled media, such as the agar plates commonly used in microbiology laboratories). In another preferred embodiment, the medium further comprises a tetrazolium dye. It one preferred embodiment, the enteric bacteria are selected from the group consisting of verotoxin-producing or verotoxin non-producing $E.$ $coli$ and Salmonella.

In yet another embodiment, the present invention comprises a method for the growth of bacteria comprising the steps of: inoculating a medium wherein the medium comprises a nutrient base, and two or more carbon sources selected from the group comprising propionic acid, methyl-glucuronide, lactose, D-malic acid, L-galactonic acid lactone, D-galacturonic acid, itaconic acid, tricarballylic acid, α-keto-butyric acid, D-aspartic acid, glucosaminic acid, citric acid, threonine, para-hydroxyphenylacetic acid, ethanolamine, N-acetylmannosamine, and tyramine; incubating the medium under conditions wherein bacteria can grow; and examining the medium for the presence of bacteria.

In one embodiment of this method, the nutrient base comprises one or more compounds selected from the group consisting of peptones, extracts, infusions, amino acids, vitamins, nitrogen, phosphorus, sulfur, magnesium, manganese, iron, and potassium. It is also contemplated that the medium of this method further comprises one or more compounds selected from the group comprising chromogenic galactosidase substrates, chromogenic glucuronidase substrates, and tetrazolium dyes.

As with the other embodiments of the present invention, it is also contemplated that the medium used in this method of the present embodiment will be useful in various formats. For example, in one embodiment, the medium is a broth. In an alternative embodiment, the medium comprises a gelling agent. Thus, the present invention contemplates various forms of the media of the present invention, ranging from broths (i.e., liquid or fluid), semi-solid (i.e., thickened or viscous liquids), to solid media (i.e., gelled media, such as the agar plates commonly used in microbiology laboratories). In another preferred embodiment, the medium further comprises a tetrazolium dye. It a particularly preferred embodiment, the enteric bacteria are selected from the group consisting of verotoxin-producing or verotoxin non-producing E. coli and Salmonella.

It is also contemplated that the method of the present invention will further comprise the step of examining the medium for the presence of enteric bacteria. In yet another embodiment, the method further comprises the step of enumerating bacteria present on the medium.

The present invention also comprises a method for enriching for the presence of one strain of bacteria in a test sample suspected of containing multiple strains of bacteria, comprising the steps of inoculating a medium with a test sample, wherein the medium comprises propionic acid; and incubating the inoculated medium under conditions wherein one species of bacteria can grow and the other species of bacteria cannot grow.

The present invention also comprises a method for the enrichment for the presence of enteric bacteria in a test sample suspected of containing multiple strains of bacteria, comprising the steps of inoculating a medium comprising one or more carbon source, one or more inhibitable chromogenic substrate, and a nutrient base, and incubating the inoculated medium under conditions wherein enteric bacteria can grow and other bacteria cannot grow. In one embodiment, the nutrient base comprises one or more compounds selected from the group comprising peptones, extracts, infusions, amino acids, vitamins, nitrogen, phosphorus, sulfur, magnesium, manganese, iron, and potassium. In another embodiment, the one or more inhibitable chromogenic substrate is selected from the group comprising galactosidase substrates, glucuronidase substrates, and tetrazolium dyes. In a particularly preferred embodiment of this method, the carbon source is selected from the group consisting of propionic acid, methyl-glucuronide, lactose, D-malic acid, L-galactonic acid lactone, D-galacturonic acid, itaconic acid, tricarballylic acid, α-keto-butyric acid, D-aspartic acid, glucosaminic acid, citric acid, threonine, para-hydroxyphenylacetic acid, ethanolamine, N-acetylmannosamine, and tyramine. In another preferred embodiment, the medium further comprises one or more compounds selected from the group consisting of sorbitol, arabitol, and cellobiose.

DESCRIPTION OF THE INVENTION

The present invention is predicated in part on the discovery that various organisms may be differentiated based on differential biochemical reactions observed in a microbiological medium. The multiple test medium of the present invention permits presumptive and rapid microbiological screening of gastrointestinal samples, water, feed, and food, without requiring inoculation of multiple agar media or the performance of additional confirmatory testing, saving both time and money. The medium of the present invention permits the inoculation of one plate with subsequent presumptive identification of such pathogens as E. coli 0157:H7 and Salmonella. This is in contrast to current methods requiring the inoculation of several media commonly used for analysis and selective isolation of the various organisms associated with gastrointestinal disease (see e.g., Baron and Finegold, at 83). As discussed above, these non-selective, selective and/or differential media permit the growth of some organisms, but each medium has significant drawbacks. Indeed, until the present invention, it has not been possible to use a simple medium with high selectivity and specificity for E. coli 0157:H7.

The present invention is based upon a novel approach to isolation and presumptive identification of E. coli 0157:H7, as well as other pathogenic E. coli serotypes, and Salmonella. Furthermore, the present invention selectively inhibits other organisms that are normal fecal flora.

The present invention was developed in a complex, multivariant, stepwise fashion, with important media components tested in varying concentrations and the reactions of various organisms observed. First, as virtually all E. coli 0157:H7 isolates are known to be lactose-positive, but negative for utilization of other commonly used carbon sources such as sorbitol, arabitol, and glycerol, chromogenic media were tested with lactose-positive isolates, to determine whether the chromogenic reaction might be inhibitable if other carbon sources in the medium were utilized. It was thought that if E. coli 0157:H7 does not use these other carbon sources, the chromogenic reaction should not be inhibited for E. coli 0157:H7 isolates, but would be inhibited for other E. coli serotypes and other lactose-positive bacteria.

In the course of developing the medium of the present invention, several very important and unexpected observations were made. For example, it was found that utilization of propionic acid was primarily restricted to the genera Escherichia, Salmonella, and Citrobacter. In addition, utilization of itaconic acid was primarily found in the genus Salmonella. Other carbon sources such as tricarballylic acid, D-aspartic acid, D-glucosaminic acid and citric acid were also found to be beneficial. Moreover, the additional surprising observation was made that media containing a sufficient level of propionic acid (e.g., 2.5 g/l) also inhibit a wide range of Gram-positive bacteria, as well as P. aeruginosa. This is significant, as P. aeruginosa is a non-glucose fermenting, Gram-negative organism commonly isolated from food, water and other liquids, that can utilize propionic acid. The present invention demonstrates several ways in which propionic acid can be combined with other nutrients and chromogenic chemicals to produce highly selective and differential media for growth, isolation, and differential identification of E. coil and Salmonella species in general, as well as E. coli 0157:H7 and other verotoxin-producing scrotypes of E. coli of clinical importance. For example, the present invention provides a means to distinguish between E. coli 0157:H7 and other verotoxin-producing E. coli serotypes. It also provides a general means to distinguish between pathogenic E. coli serotypes and non-pathogenic serotypes.

In addition, the present invention provides selective and differential media for growth, isolation and preliminary identification of Salmonella. This is a significant improvement over the media of the prior art, as all of these prior media suffer from drawbacks which prevent the detection of all Salmonella species or serogroups. As there is substantial variability within isolates of the Salmonella species and serogroups, one of the main reasons for this failure is that each medium is based on a single property of Salmonella (e.g., hydrogen sulfide production in most agars, and 1,2-propanediol fermentation in Rambach agar). It is impossible to detect all Salmonella serogroups based on a single property.

The present invention comprises a novel approach, as it combines several useful carbon sources, each of which is beneficial for the isolation of at least one Salmonella serogroup. For example, propionic acid and itaconic acid were found to be highly beneficial. As indicated above, propionic acid enriches for Salmonella, Escherichia, and Citrobacter, as it selects against most other organisms. Itaconic acid utilization is highly specific to the most commonly isolated Salmonella serogroup, Salmonella enterilidis. Additional carbon sources were then added, until a formulation was achieved that was capable of detecting all Salmonella species and serogroups calorimetrically through use of a tetrazolium redox indicator.

It is also contemplated that additional tests useful for definitive identification and differentiation of bacterial species can and will also be used in conjunction with the medium of the present invention. For example, catalase, oxidase, PYR hydrolysis, and especially indole spot tests, as well as other tests useful in differentiation of bacterial species may be used. It is not intended that the present invention be limited to the particular spot test systems disclosed in the following examples.

It is also contemplated that other agar substitutes and gelling agents (e.g., gellan, carrageenans, alginates, guar, xanthan and other gums [e.g., WO 82/02563], etc.), as well as the pectin-based products disclosed in U.S. Pat. Nos. 4,241,186 and 4,282,317 issued to Roth, hereby incorporated by reference, could be used in the present invention. Such substitutes may decrease the use of expensive chemicals and would also permit ready use of pour plate, rather than streak plate methods in situations where such methods are desirable. Such modifications may also facilitate use of this medium with water and other liquid samples, especially those of environmental origin.

It is further contemplated that the medium of the present invention will be used in various formats in addition to petri plates, such as devices which facilitate collection and inoculation of microbiological media. For example, it is contemplated that the medium will be used in existing and new dip paddle configurations such as that used in the "Diaslide," as described by M. Rosenberg et al., "Initial testing of a novel urine culture device," J. Clin. Microbiol., 30:2686 (1992). It is contemplated that the media of the present invention can be substituted for the CLED or MacConkey or EMB of the device. It is also contemplated that the medium will be used with the "Uricult-Trio," a device that is quite similar to the "Diaslide," (described by F. Dalet and T. Segovia, "Evaluation of a new agar in Uricult-trio for rapid detection of Escherichia coli in urine," J. Clin. Microbiol., 33:1395–1398 [1995]). Thus, it is contemplated that the medium of the present invention may be used in these formats with liquid or other fluid samples (e.g., water, milk, wastewater, diarrheal material, etc., and any setting in which enteric pathogens such as E. coli and Salmonella may be isolated).

It is also contemplated that the medium of the present invention will be used in other kit formats, such as that described in European Patent Appln. 79400638.7 to Rambach, which describes a test kit for growth and identification of E. coli. In this embodiment, the medium of the present invention would be substituted in the device for the medium described by Rambach. It is further contemplated that the medium of the present invention will be useful in other test kit systems, such as "Hygicult®," available from Orion Diagnostica (Espoo, Finland; this product is distributed in the United States by Gene-Trak Systems Corp., Framingham, Mass.), and Paddle Testers (Hach Co., Loveland, Colo.).

It is also contemplated that the medium of the present invention will be useful in other forms, including broth and semi-solid preparations. For example, it is contemplated that the medium of the present invention will be used in such methods as membrane filtration of water and other liquids or fluids. It is contemplated that the membrane used to filter such liquid samples will be placed in contact with the medium of the present invention, and any organisms present on the filter will be allowed to grow. It is also contemplated that the medium of the present invention will be useful in such formats as the Millipore Sampler (Millipore Corp., Bedford, Mass.), MicroSure (Gelman Sciences, Ann Arbor, Mich.), and Qualture (FMTI, Inc., West Palm Beach, Fla.). It is further contemplated that the medium of the present invention will be useful in such applications as "touch," "contact" or "swipe" testing of surfaces, wherein a surface is directly placed in contact with the medium (e.g., using Rodac plates such as those commercially available from Fisher). In this manner, any organisms present on the surface are transferred to the medium and are allowed to grow.

Thus, it is not intended that the medium of the present invention be limited to a solid preparation dispensed in any particular format such as petri plates. Indeed, it is contemplated that the medium of the present invention will be useful in numerous formats.

It is also contemplated that the medium of the present invention will be utilized in combination with other methods, including methods based on immunodetection and molecular analysis (e.g., polymerase chain reaction (PCR) amplification of organisms in a sample), to detect the presence of E. coli 0157:H7 in such samples as retail fresh meats and poultry. One method, described by M. P. Doyle and J. L. Schoeni, "Isolation of Escherichia coli 0157:H7 from retail fresh meats and poultry," J. Clin. Microbiol., 53:2394–2396 [19897]) utilizes selective enrichment, filtration of enrichment culture through hydrophobic grid membrane filters, incubation of the filters on nitrocellulose paper on selective agar, preparation of an immunoblot, selection from the filters of immunopositive colonies, screening of isolates by a Biken test for metabolites and antiserum to E. coli 01 57:H7 culture filtrate, and confirming the identification of E. coli 0157:H7 isolates by biochemical, serological and Vero cell cytotoxicity tests. It is contemplated for example, that the medium of the present invention will be used as the medium to enrich the sample for E. coli 0157:H7.

It is also contemplated that the present invention will be utilized in methods such as ELISA in combination with enrichment (see e.g., N. V. Padhye and M. P. Doyle, "Rapid procedure for detecting enterohemorrhagic Escherichia coli 0157:H7 in food," Appl. Environ. Microbiol., 57:2693–2698 [1991]; and A. J. G. Okrend et al., "An improved screening method for the detection and isolation of Escherichia coli 0157:H7 from meat, incorporating the 3M Petrifil™ test kit—HEC—for hemorrhagic Escherichia coli 0157:H7," J. Food Protect., 11:936–940 [1990]).

It is also contemplated that the media of the present invention will be useful in other forms, including enrichment broths and semi-solid preparations. Thus, it is contemplated that the present invention will be utilized in various formats, including enrichment for E. coli 0157:H7 and/or Salmonella, as well as for primary isolation and identification of these organisms obtained from clinical, veterinary, food, water and other samples.

It is further contemplated that in addition to the chromogenic substrates disclosed in the following Examples, other substrates will be utilized in the present invention. For example, it is contemplated that substrates with fluorogenic or luminogenic components will also be utilized in the present invention. It is not intended that the present invention be limited to a particular substrate, whether it be chromogenic, fluorogenic, luminogenic, or any other type used in detection systems.

It is also contemplated that the colors of the bacterial colonies could be made to vary, depending upon the chromogenic compounds used. Here again, many chromogens are now commercially available and others will undoubtedly become available in the future. Thus, any combinations of enzyme substrates and colors can be used in the medium of the present invention.

It is also contemplated that other enzyme test systems will be incorporated in the medium of the present invention. For example, it is foreseen that chromogenic substrates could be added for arylsulfatase and/or β-xylosidase which are useful in identifying Klebsiella and Enterobacter species (see e.g., J. L. Sepulveda, "Rapid presumptive identification of Gram-negative rods directly from blood cultures by simple enzymatic tests," J. Clin. Microbiol., 28:177–181 [1990]; and U.S. patent application Ser. No. 08/236,324, herein incorporated by reference), and C8-esterase, which is useful in identifying Salmonella species (A-M Freydiere and Y. Gille, "Detection of salmonellae by using Rambach agar and by a C8 esterase spot test," J. Clin. Microbiol., 29:2357–2359 [1991]). Other useful chromogenic substrates may be employed, and the scope of the current disclosure is not limited to those named above.

It is further contemplated that the medium of the present invention may modified to be even more highly selective and differential. For example, to make the medium even more selective for Gram-negative bacteria, compounds such as bile salts, deoxycholate, sodium dodecyl sulfate, tergitol-4, tergitol-7, crystal violet, brilliant green, pyronin Y, bromate, bromide, tellurite, tetrathionate, sulfamandelate, cefixime, or other selective agents such as surface-active agents, dyes, inorganic compounds, antimicrobials, etc., can be included, in order to make the medium even more selective.

It is further contemplated that the medium of the present invention can be modified by changing the nutrient and salt composition. As described in the present disclosure, many options are satisfactory. Chloride salts could be substituted for sulfate salts. In addition, many different combinations of peptones and extracts are satisfactory, although the preferred nutrients have been highly optimized.

Finally, it is further contemplated that the medium of the present invention can be modified by omitting one or more of the useful components. This may be of particular benefit in applications where it is important to lower the cost of the medium. For example, in some applications, it may not be necessary to distinguish all of the bacterial species described, and in that case a simplified and less expensive medium can be devised by omitting components that are not necessary.

From the above, it is clear that the present invention provides a highly useful medium for the rapid and reliable isolation and differentiation of various Escherichia and Salmonella species, subspecies, and even serotypes. It is also clear that the method of the present invention provides an easy to use method for the rapid and reliable differentiation of various bacteria. The medium of the present invention provides significant advantages over other media, as E. coli O157:H7, other E. coli serotypes, and other Escherichia species and Salmonella spp. grow well and are distinguishable from each other, as well as other bacterial species. The present invention therefore, fills a need for media which can provide rapid presumptive identification which can point to a particular treatment regimen based on the etiologic agent of a patient's infection.

It is also clear that the present invention provides a highly useful medium for the rapid and reliable isolation and differentiation of organisms important in the water, food and dairy industries. This is of particular importance in view of the requirements for microbial testing mandated by the federal and state governments. By providing media which permit such rapid and reliable isolation and differentiation of such pathogens as E. coli O157:H7 and Salmonella, the present invention represents a significant contribution to the public health and welfare.

DETAILED DESCRIPTION OF THE INVENTION

The present invention contemplates various media that are useful in the growth, isolation and identification of bacteria. These media and methods are particularly targeted toward the pathogenic E. coli serotypes (e.g., E. coli O157:H7, E. coli O26:H11, and O111:H8), as well as the members of the genus Salmonella. As indicated in the Experimental section below, initial investigations were directed toward the development of solid plated media containing chromogenic chemistries to test biochemical reactions useful in identifying these organisms.

As microbiologists and media developers have long recognized, it is very difficult to successfully combine multiple test reactions in one medium. In the present invention, the inclusion of propionic acid was found to be highly beneficial, as it inhibited the commensal organisms commonly associated with environmental, fecal and other gastrointestinal samples, while permitting differential identification of the pathogens of interest. This inhibition is of great importance, as it permits the use of the present invention as an enrichment tool. In the present invention, the pathogens are encouraged to grow and produce distinguishable colony colors, while the non-pathogens either do not grow on the medium, or their colonies are readily distinguishable from the pathogens.

In one embodiment of the present invention, well-isolated colonies of E. coli O157:H7 grow as very distinctive black colonies, while other verotoxin-producing E. coli serotypes grow as purple or blue colonies, and non-verotoxin-producing E. coli (i.e., ATCC 11775) grow as red colonies.

In another embodiment of the present invention, Salmonella grow as purple colonies. Importantly, and unlike other media selective for Salmonella, S. typhi and S. paratyphi A grow well on the medium of the present invention and produce distinctively colored colonies. In a preferred embodiment, the Salmonella colonies are a dark color (i.e., black, indigo, purple, blue, or green), or any color which is easily distinguishable from other organisms. It is contemplated that various tetrazolium and other dyes will be used to produce these colors, including the tetrazolium indicators described in U.S. Pat. No. 4,235,964, the disclosure of which is hereby incorporated by reference.

In contrast to the coloration of these pathogenic organisms, the limited number of non-pathogens that are capable of growing on the medium of the present invention do not grow readily, and those that do grow produce gray, yellow, orange, white or non-colored colonies. These colonies are readily distinguishable from the colonies of the pathogens.

In addition to standard streak plate methods, the media and methods of the present invention may be used with various microbiological testing techniques (e.g., the pour plate methods, filtration methods and devices, and dip paddles commonly used in dairy, food and water microbiological analyses). It is also contemplated that the medium of the present invention will be used in conjunction with such products as Petrifilm (commercially available from 3M). In these embodiments, the media of the present invention will be incorporated into the medium coating the absorbent gel or dry rehydratable film.

Thus, the media are highly versatile and solve many of the problems associated with other media used for microbiological analysis. In addition, broth formulations of these media may be used for enrichment of these pathogens. Not only is the present invention suitable for use with clinical samples, it is highly suitable for veterinary, food, water, and other environmental samples.

The media of the present invention are also useful as pre-enrichment broths for use with molecular methods for detection of these pathogens (e.g., DNA hybridization, PCR, etc.), as well as immunological testing methods (e.g., ELISA, immunomagnetic separation, etc.).

Definitions

The terms "sample" and "specimen" in the present specification and claims are used in their broadest sense. On the one hand they are meant to include a specimen or culture. On the other hand, they are meant to include both biological and environmental samples. These terms encompasses all types of samples obtained from humans and other animals, including but not limited to, body fluids such as urine, blood, fecal matter, cerebrospinal fluid (CSF), semen, and saliva, as well as solid tissue. These terms also refers to swabs and other sampling devices which are commonly used to obtain samples for culture of microorganisms.

Biological samples may be animal, including human, fluid or tissue, food products and ingredients such as dairy items, vegetables, meat and meat by-products, and waste. Environmental samples include environmental material such as surface matter, soil, water and industrial samples, as well as samples obtained from food and dairy processing instruments, apparatus, equipment, disposable and non-disposable items. These examples are not to be construed as limiting the sample types applicable to the present invention.

Whether biological or environmental, a sample suspected of containing microorganisms may or may not first be subjected to an enrichment means to create a "pure culture" of microorganisms. By "enrichment means" or "enrichment treatment," the present invention contemplates (i) conventional techniques for isolating a particular microorganism of interest away from other microorganisms by means of liquid, solid, semi-solid or any other culture medium and/or technique, and (ii) novel techniques for isolating particular microorganisms away from other microorganisms. It is not intended that the present invention be limited only to one enrichment step or type of enrichment means. For example, it is within the scope of the present invention to, following subjecting a sample to a conventional enrichment means, subjecting the resultant preparation to further purification such that pure or substantially pure cultures of a strain of a species of interest are produced. This pure culture may then be analyzed by the medium and method of the present invention.

As used herein, the terms "microorganism" and "organism" are used to refer to any species or type of microorganism, including but not limited to bacteria, yeasts and other fungi, and protozoans.

As used herein, the term "culture" refers to any sample or specimen which is suspected of containing one or more microorganisms. "Pure cultures" are cultures in which the organisms present are only of one genus and species. "Mixed cultures" are cultures in which more than one genus and/or species of microorganism are present.

As used herein, the term "enteric bacteria" refers to any genus, species, subspecies, serotype, strain, or any other taxonomic designation attributed to any member of the Enterobacteriaceae. It is not intended that the term be limited to any particular genus or species. It is intended that this term encompass pathogenic (i.e., disease-causing), as well as non-pathogenic, opportunistic, and commensal organisms. Thus, "enteric bacteria" include, but are not limited to pathogenic *E. coli* serotypes such as verotoxin-producing *E. coli* serotypes, non-verotoxin-producing pathogenic *E. coli* serotypes, non-pathogenic *E. coli* serotypes, and Salmonella.

As used herein, the terms "microbiological media" and "culture media," and "media" refer to any substrate for the growth and reproduction of microorganisms. "Media" may be used in reference to solid plated media which support the growth of microorganisms. Also included within this definition are semi-solid and liquid microbial growth systems including those incorporate living host organisms, as well as any type of media.

As used herein, the common meaning of the "nutrient base" is contemplated, wherein a basal medium is provided for growth of organisms. Various compounds and elements may be included, including sources of hydrogen donors and acceptors, carbon, nitrogen, sulfur, phosphorus, inorganic salts, vitamins, and other growth-promoting substances. In addition, carbohydrates, various salts (including, but not limited to, calcium, magnesium, manganese, sodium, potassium, phosphorus and sulfur), and complex nutrients (including but not limited to blood, serum, and albumin) may be added to the nutrient base. It is contemplated that the nutrient base primarily comprise peptones, extracts and infusions of any source, although other compounds are usually incorporated as well.

As used herein, the common meaning of the term "peptones" is contemplated, namely a chemically indefinite term used to describe a water-soluble product obtained after hydrolysis of proteins (e.g., digestion of red meat, vegetative material or casein). The present invention contemplates the use of plant, milk (casein), and/or meat peptones. These peptones may be produced by acids or enzymes. Protein hydrolysis results in a mixture of free and polymerized amino acids (i.e., peptides) including proteoses; all may remain in solution after heating to 100° C. (J. F. MacFaddin, at p. 1). Peptones are also important for the nucleic acid fractions, minerals and vitamins they provide growing cultures.

As used herein the terms "infusion" and "extract" are used in reference to products of enzymatic digestion or other treatment of substances including, but not limited to meat, yeast, and malts. Thus, an infusion may simply be the product of exposing a particular compound to another substance or may be a complex process involving the use of heat or enzymatic digestion. A meat extract or infusion encompasses any aqueous solution of amino acids, peptones, nucleotide fractions, organic acids, minerals and vitamins. In addition, the infusion or extract may be present as a dried component of media. The term also encompasses such compounds as malt extract or wort, and yeast extract.

As used herein, the term "agar" is used in a broad, generic sense, and refers to the various grades of agar extracted from natural sources such as kelp, as well as compounds produced synthetically. Thus, encompassed within this term are all gelling compounds or agents used in microbiological media, such as alginates, carrageenans, gelatins, gellans, gums, etc., regardless of their source. It is also contemplated that agar(s) and other gelling agents used in the present invention may be obtained commercially from any supply company, such as Difco (e.g., Bacto-agar), Accumedia, BBL, Oxoid, Marcor, or any other source.

As used herein, the term "gelling agent" is used in a broad generic sense, and includes compounds that are obtained from natural sources, as well as those that are prepared synthetically. As used herein, the term refers to any substance which becomes at least partially solidified when certain conditions are met. For example, one gelling agent encompassed within this definition is Gelrite™, a gellan which forms a gel upon exposure to divalent cations (e.g., $Mg^{2+}$ or $Ca^{2+}$). Gelrite™ is produced by deacetylating a natural polysaccharide produced by *Pseudomonas elodea*, and is described by Kang et al. (U.S. Pat. Nos. 4,326,052 and 4,326,053, herein incorporated by reference).

Included within the definition are various gelling agents obtained from natural sources, including protein-based as well as carbohydrate-based gelling agents. One example is bacteriological agar, a polysaccharide complex extracted from kelp. Also included within the definition are such compounds as gelatins (e.g., water-soluble mixtures of high molecular weight proteins obtained from collagen), pectin (e.g., polysaccharides obtained from plants), carrageenans and alginic acids (e.g., polysaccharides obtained from seaweed), and gums (e.g., mucilaginous excretions from some plants and bacteria). It is contemplated that various carrageenan preparations will be used in the present invention. It is also contemplated that gelling agents used in the present invention may be obtained commercially from a supply company, such as Difco, BBL, Oxoid, Marcor, Sigma, or any other source.

It is not intended that the term "gelling agent" be limited to compounds which result in the formation of a hard gel substance. A spectrum is contemplated, ranging from merely a more thickened or viscous colloidal suspension to one that is a firm gel. It is also not intended that the present invention be limited to the time it takes for the suspension to gel.

As used herein the term "gel-initiating agent" refers to any compound or element which results in the formation of a gel matrix, following exposure of a gelling agent to certain conditions or reagents. It is intended that "gel-initiating agent" encompass such reagents as cations (e.g., $Ca^{2+}$, $Mg^{2+}$, and $K^+$). Until the gelling agent contacts at least one gel-initiating agent, any suspension containing the gelling agent remains "ungelled" (i.e., there is no thickening, increased viscosity, nor hardening of the suspension). After contact, the suspension will become more viscous and may or may not form a rigid gel (i.e., contact will produce "gelling").

As used herein, the term "selective media" refers to media which support the growth of particular organisms of interest but inhibit other organisms. Such inhibition may result due to medium constituents such as compounds which are selectively toxic, as well as the end-products of microbial metabolism produced by organisms which utilize the medium constituents.

As used herein, the term "differential media" refers to media which support the growth of various organisms, but permit visual differentiation between the different genera or species. For example, a carbohydrate and pH indicator may be included in a differential medium. If an organism is capable of fermenting the carbohydrate and lowering the pH in the medium, a color change will occur. If on the other hand an organism is incapable of fermenting the carbohydrate, the pH will not be lowered and the color will not change. It is contemplated that the colony characteristics will permit differentiation as well. For example, one organism may produce a red colored colony on the medium while another species will be observed as a blue, colorless, or white colony. While some media are either selective or differential, some media are both selective and differential. Examples of media with characteristics of both selective and differential media include such media as eosin methylene blue ("EMB") and MacConkey, both of which contain compounds which inhibit gram-positive organisms, while allowing most Gram-negative organisms to grow and produce colored colonies due to the utilization of medium constituents.

As used herein, the term "chromogenic" compound refers to any compound useful in detection systems by their light absorption or emission characteristics. The term is intended to encompass any enzymatic cleavage products, soluble, as well as insoluble, which are detectable either visually or with optical machinery. Included within the designation "chromogenic" are all enzymatic substrates which produce an end product that is detectable as a color change. Thus, a "chromogenic substrate" is an enzymatic substrate that will permit the production of a detectable color upon reaction of an enzyme on the substrate. This includes, but is not limited to any color, as used in the traditional sense of "colors," such as indigo, blue, purple, black, red, yellow, green, orange, brown, etc., and any combination of these (e.g., purple/red, blue/green, etc.), as well as fluorochromic or fluorogenic compounds, which produce colors detectable with fluorescence (e.g., the yellow-green of fluorescein, the red of rhodamine, etc.). It is intended that such other indicators as dyes (e.g., pH) and luminogenic compounds be encompassed within this definition.

As used herein, the term "inhibitable chromogenic substrate" or "chromogenic substrate that is inhibitable," is used in reference to chromogenic substrates which do not result in the production of a color due to the presence or formation of compounds which inhibit color production. This inhibition may be due to any of a variety of means, including but not limited to, suppression or inhibition of enzymatic or metabolic activity, or inhibition of color production due to interference with other compounds present, or chemical reactions occurring in the medium.

As used herein, the term "diffusible pigment" refers to the production and release of pigmented (i.e., colored) substances from bacterial cells and colonies. When grown on microbiological medium, diffusible pigments are often observable, as they may impart a color to the medium. For example, pyocyanin is a diffusible pigment produced by most *P. aeruginosa* strains, which colors the medium surrounding colonies of this organism a green color. This green color may range from a yellow-green to a blue-green or turquoise, depending upon the strain and the medium constituents. There are numerous diffusible pigments produced by various organisms. It is not intended that the present invention will be limited to pyocyanin or any other specific diffusible pigment.

As used herein, the terms "diffuse" and "localized" pigmentation refer to the distribution of pigment through the medium. It is intended that the term "diffuse pigmentation" refer to the diffusion of the pigment in the medium away from the colonial source of the pigment. In contrast, the term "localized pigmentation" refers to the lack of or minimal diffusion of pigment from the colonial source. For example, the pigment is localized if it remains very close to the colonial source.

As used herein, the term "swarming" is used in reference to the growth of Proteus on media, in particular semi-solid or solid plated agar. Swarming is a phenomenon associated with motile organisms, particularly *P. mirabilis,* in which a group of organisms moves outwards from the colony as a unified mass. Often, the growth on solid media appears as a series of concentric rings surrounding the colony, usually shaped like a target. While Proteus is often associated with swarming growth, it is contemplated that other organisms grown on the medium of the present invention may exhibit swarming. It is also contemplated that the swarming of such organisms may be inhibited by the medium of the present invention.

As used herein, the term "spreading" is used in reference to the colony morphology of some organisms, in which the colony edges are not smooth or "entire." Rather, when viewed either by eye or through a dissecting microscope, the edges of the colonies are usually irregular. The usual meaning of the word is contemplated, as used by those skilled in the art of observing bacterial colony morphology. For example, it is contemplated that some organisms, including but not limited to *P. mirabilis* will exhibit some degree of spreading colony morphology on the medium of the present invention.

As used herein, the term "primary isolation" refers to the process of culturing organisms directly from the sample. Thus, primary isolation involves such processes as inoculating an agar plate from a culture swab taken from any site (e.g, samples such as rectal swabs, as well as swabs from environmental locations such as machinery, equipment, floors, etc.) or other samples (e.g., fecal samples, urine, blood, water, food, feed, etc.). Primary isolation may also be done in liquid or semi-solid media.

As used herein, the term "presumptive diagnosis" refers to a preliminary diagnosis which gives some guidance to the treating physician as to the etiologic organism involved in the patient's disease. Presumptive diagnoses are often based on "presumptive identifications," which as used herein refer to the preliminary identification of a microorganism based on observation such as colony characteristics, growth on primary isolation media, gram stain results, etc.

As used herein, the term "definitive diagnosis" is used to refer to a final diagnosis in which the etiologic agent of the patient's disease has been identified.

As used herein, the term "verotoxin-producing" refers to serotypes or isolates of *E. coli* which produce verotoxin. In contrast, the term "non-verotoxin producing" refers to serotypes or isolates of *E. coli* which do not produce verotoxin.

Experimental

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); μM (micromolar); N (Normal); mol (moles); mmol (millimoles); μmol (micromoles); nmol (nanomoles); g (grams); mg (milligrams); μg (micrograms); ng (nanograms); l or L (liters); ml (milliliters); μl (microliters); cm (centimeters); mm (millimeters); μm (micrometers); nm (nanometers); ° C. (degrees Centigrade); SDS (sodium dodecyl sulfate); ELISA (Enzyme-Linked Immunosorbent Assay); TSA (trypticase soy agar); EMB (eosin methylene blue medium); MacConkey (MacConkey medium); RA or Ra (Rambach agar; E. Merck, Darmstadt, Germany); CLED (cystine lactose electrolyte deficient agar); salmon-glc, or Sal-glc (salmon-beta-D-glcA; 6-chloro-3-indolyl-β-D-glucuronic acid, monocyclohexylammonium salt, Biosynth); X-gal (5-bromo-4-chloro-3-indolyl-β-D-galactoside, Biosynth); Ind-gal (indoxyl-β-D-galactoside, Biosynth); Bluo-gal (5-bromo-3-indolyl-β-D-galactoside, Chembridge Corp., Northbrook, Ill.); proteose peptone #3 (Proteose Peptone #3, Difco); PP (proteose peptone, Difco); CE90MX (casein peptone, Deltown); soy peptone or "HySoy" (Quest International, Norwich, N.Y.); yeast extract (Oxoid); Redigel (RCR Scientific, Goshen, Ind.); Accumedia (Accumedia, Baltimore, Md.); Oxoid (Oxoid, Basingstoke, England or Oxoid, Columbia, Md.); BBL (Becton Dickinson Microbiology Systems, Cockeysville, Md.); DIFCO or Difco (Difco Laboratories, Detroit, Mich.); Remel (Remel, Lenexa, Kans.); Marcor (Marcor Development, Hackensack, N.J.); bioMeeriux (bioMériéux S.A., Montalieu-Vercieu, France or bioMerieux-Vitek, Hazelwood, Mo.); Scientific Products (McGaw Park, Ill.); Fisher (Fisher Scientific, New York, N.Y.) Sigma (Sigma Chemical Co., St. Louis, Mo.); Biosynth (Biosynth AG, Skokie, Ill.); Pfanstiehl (Pfanstiehl Laboratories, Inc., Waukegan, Ill.); Deltown (Deltown Chemurgic, Greenwich, Conn.); and 3M (3M, St. Paul, Minn.).

In the experimental section that follows, unless otherwise specified, the L-form of all amino acids was used. In addition, unless otherwise specified, all acidic carbon sources were adjusted to pH 6–8, prior to their addition to the media formulations. Also, unless otherwise specified, the chemical reagents (e.g., $Na_2HPO_4$, $KH_2PO_4$, $MgSO_4$, D-arabitol, α-D-lactose, D-sorbitol, D-cellobiose, glycerol, tetrazolium violet, etc. were obtained from Sigma or Pfanstiehl. Agar was obtained from Accumedia. Chromogenic substrates were obtained from Biosynth, except for Bluogal, which was from Chembridge Corp. The following Table lists the principal bacterial strains used in the following Examples. Additional species and strains representing the Enterobacteriaceae, various gram-positive and numerous other organisms not shown in this Table were also tested.

TABLE 6

Principal Bacteria Strains Tested

| Organism | Source and Number |
| --- | --- |
| *Citrobacter genospecies* 11 | Biolog 13660 |
| *C. sedlakii* | Biolog 13653 |
| *Escherichia coli* | ATCC 11775 (same as Biolog 287) |
| *E. coli* 0157:H11 | Biolog 11547 |
| *E. coli* 026:H11 | Biolog 13664 |
| *E. coli* 026:H11 | Biolog 13665 |
| *E. coli* 0111:H8 | Biolog 13662 |
| *E. coli* 0111:H8 | Biolog 13663 |
| *Enterobacter amnigenus* | Biolog 2991 |
| *E. asburiae* | Biolog 1806 |
| *Enterobacter agglomerans* biogroup 4 | Biolog 11516 |
| *Enterobacter agglomerans* biogroup 5 | Biolog 11517 |
| *Enterobacter hormaechei* | Biolog 11538 |
| *Erwinia carotovora* ss *carotovora* | Biolog 8038 |
| *Klebsiella pneumoniae* | Biolog 5008 |
| *K. oxytoca* | Biolog 1046 |
| *Lecleria adecarboxylata* | Biolog 3228 |
| *Pseudomonas aeruginosa* | ATCC 10145 (same as Biolog 8512) |
| *Salmonella enteritidis* | Biolog 7320 |
| *Salmonella choleraesuis* | ATCC 13312 (same as Biolog 9927) |
| *S. paratyphi* A | Biolog 1809 |
| *S. paratyphi* C | Biolog 5546 |
| *S. typhi* | Biolog 4076 |
| Salmonella SS2 (*S. salamae*) | Biolog 13610 |

TABLE 6-continued

Principal Bacteria Strains Tested

| Organism | Source and Number |
|---|---|
| Salmonella SS3 (*S. arizonae*) | Biolog 4061 |
| Salmonella SS4 (*S. houtenae*) | Biolog 13609 |
| Salmonella SS5 (*S. bongori*) | Biolog 13669 |
| Salmonella SS6 (*S. enterica* ss indica) | Biolog 13670 |
| *Serratia plymuthica* | Biolog 4326 |
| *Shigella sonnei* | Biolog 5557 |

EXAMPLE 1

Inhibition of X-Gal Utilization

In this experiment, the inhibition of X-gal utilization due to acid production or preferential carbon source utilization during microbial metabolism was investigated. This was important in the development of the medium of the present invention. Utilization of an alternative carbon source was investigated as a tool for use in the design of a medium in which colonial color production is inhibited or enhanced. For example, if an organism utilized D-sorbitol to produce acid, this might inhibit the production of colored colonies by either inhibiting utilization of X-gal (i.e., the organisms preferentially utilize D-sorbitol rather than X-gal), or by interfering with the mechanism of color production from X-gal utilization.

A basal medium was prepared by dissolving agar (15 g/l), CE90 MX (10 g/l), $Na_2SO_4$ (2.5 g/l), $MgSO_4$ (0.6 g/l) and X-gal (100 mg/l) in one liter of distilled water. This basal medium was divided into three batches, each batch containing an additional ingredient. Batch #1 contained 10 g/l D-sorbitol; batch #2 contained 10 g/l D-arabitol; and batch #3 contained 10 g/l glycerol. Each batch was boiled in a microwave oven until the agar was completely dissolved, and dispensed into petri plates upon cooling.

Plates from each batch were streaked with organisms listed in Table 6, including *E. coli* non 0157:H7 (ATCC #11775), *E. coli* 0157:H7, *Klebsiella oxytoca*, and various Salmonella species, including *S. choleraesuis*, *S. enteritidis*, *S. paratyphi*, *S. typhi*, SS3, SS2, and SS4. After incubation at 35° C. overnight (18–24 hours), the plates were observed.

The following table shows the colonial characteristics for each of the organisms tested. In order to simplify the tables, abbreviations were used for the names of the organisms. These abbreviations were used in the subsequent examples and correlate to the following list:

| | |
|---|---|
| E.c. = | *E. coli* (ATCC #11775) |
| 0157:H7 = | *E. coli* 0157:H7 |
| S.c. = | *S. choleraesuis* |
| S.e. = | *S. enteritidis* |
| S.p. = | *S. paratyphi* |
| S.t. = | *S. typhi* |
| SS3 = | SS3 (*S. arizonae*) |
| SS2 = | SS2 (*S. salamae*) |
| SS4 = | SS4 (*S. houtenae*) |
| K.o. = | *K. oxytoca* |

This approach appeared to be promising. *E. coli* and *E. coli* 0157:H7, as well as SS3 and *K. oxytoca* are lactose-positive (i.e., they are able to utilize lactose to produce acid). Therefore, these organisms would normally be expected to grow as blue-green colonies on a medium which contains X-gal. However, in the presence of D-sorbitol, the formation of blue-green color from X-gal was inhibited in the lactose-positive, sorbitol-positive strains (e.g., *E. coli* non-0157:H7, *K. oxytoca*, and SS3), but not in the lactose-positive, sorbitol-negative *E. coli* 0157:H7. Arabitol and glycerol were only partially effective in decreasing the blue-green coloration of SS3 and *K. oxytoca*, but not of *E. coli*. Thus, this formula was partially successful as a differential medium, as it was capable of differentiating between 0157:H7 and other lactose-positive bacteria, as well as from lactose-negative bacteria.

TABLE 7

Colonial Characteristics of Organisms

| | Organism: | | | | | | | | | |
|---|---|---|---|---|---|---|---|---|---|---|
| Batch | E.c. | 0157:H7 | S.c. | S.e. | S.p. | S.t. | SS3 | SS2 | SS4 | K.o. |
| 1 | Light blue-green | Blue-green | White | White | White | White | White | White | White | White |
| 2 | Blue-green | Blue-green | White | White | White | White | Light blue-green | White | White | Light blue-green |
| 3 | Blue-green | Blue-green | White | White | White | White | Very light blue-green | White | Very light blue-green | |

EXAMPLE 2

Acid Inhibition of Lactose Induced Tetrazolium Reduction

In this experiment, the effect of acid production due to utilization of D-sorbitol, D-arabitol or glycerol on lactose-induced reduction of tetrazolium was tested. A basal medium was prepared by dissolving agar (15 g/l), Difco proteose peptone (2.5 g/l), $Na_2HPO_4$ (0.7 g/l), $KH_2PO_4$ (0.3 g/l), $MgSO_4$ (0.1 g/l), and tetrazolium violet (80 mg/l). This basal medium was divided into five batches which contained additional ingredients. Batches #8 and #12 contained 10 g/l D-sorbitol and 1 g/l lactose; batch #9 contained 10 g/l D-arabitol and 1 g/l lactose; batch #10 contained 10 g/l glycerol and 1 g/l lactose; batch #11 contained 10 g/l D-sorbitol and 2 g/l lactose; batch #12 was identical to batch

8, but it contained an additional 0.7 g/l $Na_2HPO_4$, and an additional 0.3 g/l $KH_2PO_4$. The media were boiled in a microwave oven until the agar was completely dissolved, and dispensed as described in Example 1 above.

Plates from each batch were streaked with various organisms listed in Table 6, including *E. coli* (ATCC #11775), *E. coli* 0157:H7, *Klebsiella oxytoca,* and various Salmonella species, including *S. choleraesuis, S. enteritidis, S. paratyphi, S. typhi,* SS3, SS2, and SS4. After incubation overnight (18–24 hours), the plates were observed.

The following table shows the colonial characteristics for each of the organisms tested. As shown, only batches #11 and #12 produced partial selective coloration of *E. coli* 0157:H7. Batch #12 was the best overall, but the results were not as good as those obtained with batch #1 in Example 1.

EXAMPLE 4

Enhancement of Colony Coloration

In this example, various compounds were tested for their ability to enhance the differences in colony coloration between *E. coli* 0157:H7 and other species with similar metabolic properties. In this example, bluo-gal was also tested as an alternative to X-gal and Ind-gal.

A basal medium was prepared which contained agar (15 g/l), CE90 MX (5 g/l), $Na_2SO_4$ (2.5 g/l), $MgSO_4$ (0.6 g/l), $MnSO_4$ (50 mg/l), D-sorbitol (10 g/l), D-arabitol (10 g/l), and Bluo-gal (300 mg/l). This medium was divided into nine batches. With the exception of batch #1, each batch contained one or more additional ingredients, which it was thought might stimulate growth and/or the coloration of *E. coli* 0157:H7.

TABLE 8

Colonial Characteristics of Organisms

| Batch: | E.c. | 0157:H7 | S.c. | S.e. | S.p. | S.t. | SS3 | SS2 | SS4 | K.o. |
|---|---|---|---|---|---|---|---|---|---|---|
| 8 | Light purple | Light purple | Light purple | Light purple | Light purple | Light purple | Light purple | Light purple | Light purple | Light purple |
| 9 | White | White | White | White | White | White | White | White | White | Dark purple |
| 10 | Dark purple | Dark purple | Dark purple | Dark purple | Dark purple | Light purple | Dark purple | Dark purple | Dark purple | Light purple |
| 11 | Light purple | Purple | Light purple | Light purple | Light purple | Light purple | Light purple | Light purple | Light purple | Light purple |
| 12 | Light purple | Dark purple | Light purple | Light purple | Light purple | Light purple | Light purple | Light purple | Light purple | Light purple |

EXAMPLE 3

Use of Ind-gal

In this example, various concentrations of Ind-gal were tested as a potential alternative to X-gal. Of particular interest was the determination of whether Ind-gal would be more susceptible than X-gal to inhibition by sorbitol and arabitol utilization.

A basal medium was prepared by dissolving a mixture of agar (15 g/l), CE90 MX (5 g/l), $Na_2SO_4$ (2.5 g/l), $MgSO_4$ (0.6 g/l), D-sorbitol (10 g/l), and D-arabitol (10 g/l). This medium was divided into three batches, with each batch containing a different concentration of Ind-gal. Batch #1 contained 100 mg/l Ind-gal; batch #2 contained 200 mg/l Ind-gal; and batch #3 contained 300 mg/l Ind-gal. The media were microwaved and dispensed as described in Example 1.

Plates from each batch were streaked with various organisms listed in Table 6, including *E. coli* (ATCC #11775), *E. coli* 0157:H7, *Klebsiella oxytoca,* and various Salmonella species, including *S. choleraesuis, S. enteritidis, S. paratyphi, S. typhi,* SS3, SS2, and SS4. After incubation overnight (18–24 hours), the plates were observed.

On batch #1, *E. coli* 0157:H7 was gray, and non-0157:H7 *E. coli* was light yellow. On batches #2 and #3, *E. coli* 0157:H7 was black, and non-0157:H7 *E. coli* was light yellow. On batches #1–3, all of the Salmonella species, including the lactose-positive SS3, were white, and *K. oxytoca* was light yellow. Thus, the two best formulations identified in this example were batches 2 and 3. These formulae resulted in the production of black colored colonies of *E. coli* 0157:H7, that allowed ready differentiation of *E. coli* 0157:H7 from the various closely related organisms.

Batch #2 contained L-tryptophan (1 g/l); batch #3 contained sodium propionate (1 g/l); batch #4 contained sodium cyanate (200 mg/l); batch #5 contained tryptophan (1 g/l) and sodium propionate (1 g/l); batch #6 contained L-tryptophan (1 g/l) and sodium cyanate (200 mg/l); batch #7 contained sodium propionate (1 g/l) and sodium cyanate (200 mg/l); batch #8 contained tryptophan (1 g/l), sodium propionate (1 g/l), and sodium cyanate (200 mg/l); and batch #9 contained L-tryptophan (1 g/l), sodium propionate (1 g/l), and sodium cyanate (300 mg/l). These media were microwaved and dispensed as described in Example 1.

Plates from each batch were streaked with various organisms listed in Table 6, including *E. coli* (ATCC #11775), *E. coli* 0157:H7, *Shigella sonnei, Erwinia carotovora* ss *carotovora, Serratia plymuthica, Enterobacter agglomerans* biogroups 4 and 5, *E. amnigenus, E. asburiae, E. hormachei,* and *Citrobacter genospecies* 11. These species were tested because they were found to produce colored colonies on batch #1 that most closely resembled colonies of *E. coli* 0157:H7. After incubation overnight (18–24 hours) at 35° C., the plates were observed.

Overall, the specificity of Bluo-gal utilization by *E. coli* 0157:H7 appeared to be not as good as Ind-gal, but better than X-gal. Of the formulations tested, batches #4, 8, and 9 permitted the best discrimination between *E. coli* 0157:H7 and other organisms. The cyanate in batch #4 was found to be somewhat beneficial, since it inhibited *C. genospecies* 11, *E. amnigenus, E. asburiae, E. agglomerans* biogroup 4, *E. agglomerans* biogroup 5, *E. carotovora,* and *S. sonnei.* However, *E. hormachei* was not as readily distinguishable from *E. coli* 0157:H7.

In this example, a surprising and very important observation was made. The propionate in batch #3 was found to inhibit the growth of *E. agglomerans* biogroup 4, *E. amnigenus,* and *E. carotovora* ss *carotovora,* which was very beneficial in improving the specificity of this medium for *E. coli* 0157:H7.

Colonies of *E. coli* non-0157:H7 and *E. coli* 0157:H7 were also tested for indole production using the spot indole test commercially available from Remel. Both *E. coli* non-0157:H7 and *E. coli* 0157:H7 were only indole-positive on the media formulations which included supplemental tryptophan (i.e., batches #2, 5, 6, 8, and 9). Thus, if the indole test is to be used to distinguish *E. coli* from other organisms (i.e., Enterobacter) grown on this medium, the medium formulation should include tryptophan.

This example highlights the effect of propionic acid on various organisms. Not only did propionic acid support growth of *E. coli* 0157:H7, but it inhibited the growth of many organisms unable to utilize propionic acid. Thus, it also provides a significant means to enrich for Escherichia, Salmonella, and Citrobacter.

Based on these observations, the effects of differing concentrations of propionate were studied, in order to determine the optimal concentration for differentiating *E. coli* 0157:H7 from other organisms. It was found that sodium propionate concentrations in the range of 2 to 3 g/l worked even better than 1 g/l (See, Example 6).

EXAMPLE 5

Inclusion of Cellobiose and Sal-glc

In this example, various concentrations of sorbitol, arabitol, and cellobiose, were tested. Cellobiose was included because most of the species that still resembled *E. coli* 0157:H7 were cellobiose-positive, whereas *E. coli* 0157:H7 was cellobiose-negative. In addition, sal-glc was added to the medium to differentiate *E. coli* 0157:H7 (glucuronidase-negative) from other potential sorbitol-negative *E. coli* strains (glucuronidase-positive).

A basal medium was prepared by dissolving agar (15 g/l), CE90MX (1 g/l), $Na_2SO_4$ (2.5 g/l), $MgSO_4$ (0.6 g/l), $MnSO_4$ (50 mg/l), Sal-glc (100 mg/l), and Ind-gal (200 mg/l). This medium was divided into ten batches, with each batch containing at least one additional ingredient. Batches 1–5 also contained sodium propionate (3 g/l) and tryptophan (1 g/l). Batches 6–10 contained an additional 4 g/l CE90MX (for a total of 5 g/l, instead of the 1 g/l in the basal medium). These batches also contained varying concentrations of D-sorbitol, D-arabitol, and D-cellobiose. Batches #1 and #6 contained D-sorbitol (10 g/l); batches #2 and #7 contained D-sorbitol (10 g/l) and D-arabitol (10 g/l); batches #3 and #8 contained D-sorbitol (20 g/l) and D-arabitol (10 g/l); batches #4 and #9 contained D-sorbitol (10 g/l) and cellobiose (10 g/l); and batches #5 and #10 contained D-sorbitol (10 g/l), D-arabitol (10 g/l), and cellobiose (10 g/l). These media were microwaved and dispensed as described Example 1. Plates from each batch were streaked with the same organisms as in the previous example. After incubation overnight (18–24 hours) at 35° C., the plates were observed.

Batches #1, #5, and #10 produced the best results. On batch #1, *E. coli* non-0157:H7 was red, *E. coli* 0157:H7 was black, most of the other organisms were white, and *E. asburiae* and *E. agglomerans* biogroup 5 were not able to grow. On batch #5, *E. coli* non-0157:H7 was red, *E. coli* 0157:H7 was black, *E. agglomerans* biogroup 5, and *E. asburiae* were light gray, and the other organisms were white. On batch #10, *E. coli* non-0157:H7 was purple, *E. coli* 0157:H7 was black, *E. agglomerans* biogroup 5, *E. asburiae,* and *S. sonnei* were gray, and the other organisms were white. Batch #2 also provided good differentiation. On this batch, *E. coli* non-0157:H7 was red, *E. coli* 0157:H7 was black, *E. agglomerans* biogroup 5, and *E. asburiae* were gray, and the other organisms were white. Batch #3 was similar to #2, but *E. coli* non-0157:H7 was red/purple and all of the other organisms were lighter gray or white. On batch #4, *E. coli* 0157:H7 was white, and the other organisms were the same colors as on batch #2. On batch #7, *E. coli* non-0157:117 was purple, *E. coli* 0157:H7 was dark gray, and all others were dark gray except *S. plymuthica,* which was white. Batch #8 also produced good results, that were similar to batch #7, but *E. coli* non-0157:H7 was a purple color with a more intense blue aspect, and *E. coli* 0157:H7 was slightly darker. On batch #9, *E. coli* non-0157:H7 was red/purple, *E. coli* 0157:H7, *E. agglomerans* biogroup 5, and *E. asburiae* were light gray, *S. sonnei* was gray, and all other organisms were white. Batch #6 was perhaps the least optimal formulation, with colonies of *E. coli* non-0157:H7 appearing blue-purple, and *E. coli* 0157:H7, *E. agglomerans* biogroup 5, and *E. asburiae* colonies all appearing gray.

Inclusion of D-cellobiose proved to be beneficial, as batch #5 was better than batch #2, and batch #10 was better than batch #7. Furthermore, upon review of the results of this experiment, an additional unexpected and surprising observation was made. If D-arabitol was omitted (e.g., batches #4 and #9), the black coloration of *E. coli* 0157:H7 was greatly decreased (white in batch #4, light gray in batch #9). Thus, the inclusion of D-arabitol in combination with D-sorbitol and D-cellobiose was optimal.

EXAMPLE 6

Optimal Propionate Concentration

In this example, the effect of varying the propionate concentration was tested. A basal medium was prepared which contained agar (15 g/l), D-sorbitol (10 g/l), D-arabitol (10 g/l), D-cellobiose (10 g/l), CE90 MX (5 g/l), tryptophan (1 g/l), $Na_2SO_4$ (2.5 g/l), $MgSO_4$ (0.6 g/l), $MnSO_4$ (50 mg/l), $KH_2PO_4$ (100 mg), Sal-glc (100 mg/l), and Ind-gal (200 mg/l). This basal medium was divided into five batches, with each batch containing at least one additional ingredient. Batch #1 contained 2 g/l sodium propionate; batch #2 contained 3 g/l sodium propionate; batch #3 contained 2.5 g/l sodium propionate; batch #4 contained 1 g/l soy peptone and 2.5 g/l sodium propionate; and batch #5 contained 200 mg/l yeast extract, and 2.5 g/l sodium propionate. The media were microwaved and dispensed as described in Example 1.

Plates from each batch were streaked for isolation with various organisms listed in Table 6, including *E. coli* (ATCC #11775), *E. coli* 0157:H7, *E. agglomerans* biogroup 5, and *E. asburiae.* After incubation overnight (18–24 hours) at 35° C., the plates were observed for growth and colony characteristics.

All of these various media produced excellent growth and differential coloration of the *E. coli* serotypes. The non-0157:H7 *E. coli* colonies were red, and the *E. coli* 0157:H7 colonies were gray-black. However, on batch #2 (containing 3 g/l sodium propionate), there was a slight growth inhibition of the non-0157:H7 *E. coli,* and *E. coli* 0157:H7. All of these formulations strongly inhibited *E. agglomerans* biogroup 5, and *E. asburiae.*

Overall, the recipes for batches 3–5 were excellent in terms of producing colonies of *E. coli* 0157:H7 that may be readily differentiated from non-0157:H7 *E. coli* serotypes and other species.

EXAMPLE 7

Optimal Peptone Composition and Concentration

In this example, soy peptone and CE90MX were compared as peptone sources in the medium of the present invention. A basal medium was prepared which contained agar (15 g/l), $Na_2SO_4$ (2.5 g/l), $MgSO_4$ (0.6 g/l), $MnSO_4$ (50 mg/l), $KH_2PO_4$ (100 mg/l), sodium propionate (2.5 g/l), D-sorbitol (10 g/l), D-arabitol (10 g/l), cellobiose (10 g/l), tryptophan (1 g/l), Sal-glc (100 mg/l), and Ind-gal (200 mg/l). This medium was divided into twelve batches, with each of these batches containing various concentrations of soy peptone or CE90MX. Batches #1–3, contained 3 g/l, 4 g/l, and 5 g/l CE90MX, respectively. Batches #4–6 contained 3 g/l, 4 g/l and 5 g/l soy peptone, respectively. Batch #7 contained 5 g/l CE90MX and an additional 100 mg/l Ind-gal; batch #8 contained 5 g/l CE90MX and an additional 0.5 g/l sodium propionate; batch #9 contained 6.5 g/l CE90MX; batch #10 contained 8 g/l CE90MX; batch #11 contained 5 g/l CE90MX and 1.5 g/l soy peptone; and batch #12 contained 5 g/l CE90MX and 3 g9l soy peptone.

The media were microwaved and dispensed as described in the Example 1. *E. coli* (ATCC #11775), *E. coli* 0157:H7, *E. asburiae*, and *E. agglomerans* biogroup 5 were streaked on plates of each medium, incubated at 35° C. for 18–24 hours and observed for growth and colonial characteristics. Spot indole tests were also performed on colonies from batches #3, 6 and 7.

The results from the indole test of colonies grown on batches #3, 6 and 7 were excellent. The differentiation of non-0157:H7 *E. coli* and *E. coli* 0157:H7 was also excellent with *E. coli* growing as red to red/purple colonies, and *E. coli* 0157:H7 growing as black to dark gray colonies. For the batches containing CE90MX, *E. coli* 0157:H7 was slightly darker black on batch #1, than on batch #2 or #3. However, batches containing soy peptone (batches #4–6) produced darker black 0157:H7 colonies than CE90MX. Of these three batches, #6 was the best. Batch #7, with an increased concentration of Ind-gal, produced very dark *E. coli* 0157:H7. Batches #8–12 produced acceptable results, but the Enterobacter species grew too well. On batch #12, colonies of *E. coli* were red/purple, instead of red. The best formulations in this experiment were batches #6 and 7.

EXAMPLE 8

Testing of Other Verotoxin-Producing *E. coli* Serotypes and Optimization of $NaSO_4$, $MgSO_4$, and $MnSO_4$ In this example and the following three examples, various sulfate-containing compounds were tested and optimized to enhance the color differentiation between *E. coli* 0157:H7 and other *E. coli* serotypes. In addition, the selectivity of the medium against *Pseudomonas aeruginosa*, and Gram-positive organisms was tested.

A basal medium was prepared which contained agar (15 g/l), $Na_2SO_4$ (500 mg/l), $MgSO_4$ (100 mg/l), $KH_2PO_4$ (100 mg/l), CE90MX (5 g/l), sodium propionate (2.5 g/l), D-sorbitol (10 g/l), D-arabitol (10 g/l), cellobiose (10 g/l), L-tryptophan (500 mg/l), Sal-glc (120 mg/l), and Ind-gal (250 mg/l). This medium was divided into six batches, with batch #1 comprising the basal medium and batches #2–6 batches containing additional $NaSO_4$, $MgSO_4$, and $MnSO_4$. Batch #2 contained an additional 2 g/l $Na_2SO_4$; batch #3 contained an additional 2 g/l $Na_2SO_4$, as well as 50 mg/l $MnSO_4$; batch #4 contained an additional 4.5 g/l $Na_2SO_4$; batch #5 contained an additional 4.5 g/l $Na_2SO_4$, as well as 50 mg/l $MnSO_4$; batch #6 contained an additional 2 g/l $MgSO_4$.

The media were microwaved and dispensed as described in Example 1. *E. coli* (ATCC 11775), *E. coli* 026:H11, (Biolog 13664), *E. coli* 026:H11 (Biolog 13665), *E. coli* 0111:H8 (Biolog 13662), *E. coli* 0111:H8 (Biolog 13663), *E. coli* 0157:H7, *K. pneumoniae*, and *S. sonnei* (as listed in Table 6) were streaked on plates of each medium, incubated at 35° C. for 16 hours and observed for growth and colonial characteristics.

Batches #1, #2 and #4 were nearly identical, although batches #2 and #4 (with higher concentrations of $Na_2SO_4$) had slightly more localized color, and *E. coli* (Biolog ATCC 11775), and *E. coli* 026:H11 (Biolog 13664) were slightly more blue. Batch #1 had slightly more diffuse color.

In a comparison of batches #2, 3, 4 and 5, $MnSO_4$ was found to definitely result in production of more localized color with all strains. The only drawback was that *K. pneumoniae* is also a darker gray. Batches #2 and #6 were similar, but *E. coli* 0111:H8 (Biolog 13662) and 0111:H8 (Biolog 13663) were slightly lighter in color on batch #6.

Of all these batches, batch #5 was the best. The red coloration of *E. coli* was improved somewhat by $MnSO_4$. Without $MnSO_4$, the colonies turn purple at 36 hours of incubation. Batch #1 was better than batch #5 for *S. sonnei*, which was inhibited somewhat by $MnSO_4$ and/or $Na_2SO_4$.

EXAMPLE 9

This example was a continuation of Example 8, with the exception that *E. coli* 0157:H7 was streaked for well-isolated colonies. The same basal medium was prepared as described in Example 8. This medium was used for batches #1 and #2, with the only difference being that for batch #1 16 ml of medium were poured into the plates, and 20 ml of medium were poured into the plates for batch #2. Batch #3 and #4 both contained 50 mg/l $MnSO_4$. For batch #3, 16 ml plates were poured; for batch #4, 20 ml plates were poured. Batches #5 and #6 were the same, with an additional 4.5 g/l $Na_2SO_4$ and 50 mg/ml $MnSO_4$. Batch #5 contained 16 ml of medium per plate and batch #6 contained 20 ml of medium per plate. After the media were microwaved and dispensed as described in Example 1, the plates were streaked for isolation with *E. coli* 0157:H7.

Following incubation at 35° C. for 16 hours, the plates were observed for growth. Of these batches, #5 was the best, as it resulted in the most rapid production of color, and the darkest black colony coloration.

EXAMPLE 10

This example was a continuation of Examples 8 and 9. In this example, batch #5 of Example 9 was used to test the selectivity of the medium against various Gram-positive organisms and *P. aeruginosa*. These organisms were chosen for testing as they all tested positive for lactose and/or propionate.

Plates of medium from batch #5 of Example 9 were streaked for isolation with *Enterococcus casseliflavus* (Biolog #13461), *Staphylococcus epidermidis* B (Biolog #12355), *Staphylococcus felis* (Biolog #11457), *Streptococcus canis* (Biolog #11111), *Streptococcus pneumoniae* (Biolog #11133), CDC A-4B (Biolog #10322), *Bacillus polymyxa* (Biolog #9259), and *P. aeruginosa* (Biolog #8512). Following incubation at 35° C. for 24 hours, these plates were observed for growth. Surprisingly, none of these organisms were able to grow on this medium. This was a very important and beneficial finding, as it shows that this medium is very good at selecting against Gram-positive organisms and P. aeruginosa.

EXAMPLE 11

This example also was a continuation of Examples 8–10. In this example, the medium of batch #5 from Example 9 was tested with various verotoxin-producing and non verotoxin-producing E. coli serotypes.

For clarity the recipe of this medium is shown here. The medium contained agar (15 g/l), D-sorbitol (10 g/l), D-arabitol (10 g/l), cellobiose (10 g/l), CE90MX (5 g/l), sodium propionate (2.5 g/l), L-tryptophan (500 mg/l), $Na_2SO_4$ (5 g/l), $MgSO_4$ (100 mg/l), $KH_2PO_4$ (100 mg/l), $MnSO_4$ (50 mg/l), Sal-glc (120 mg/l), and Ind-gal (250 mg/l). The medium was microwaved and dispensed as previously described. The plates were then streaked for isolation with various E. coli serotypes. The following table shows the serotypes tested. This table also shows the colony colors observed for each serotype. Notably, the coloration was slightly different depending upon how crowded together the individual colonies were on the plate. For the areas with confluent colonies, it was not possible to visually distinguish between individual colonies. For areas with crowded colonies, the colonies grew very closely together, but it was possible to visually distinguish individual colonies. For single colonies, the colonies grew as isolated colonies, well-separated from other colonies on the plate.

TABLE 9

| | | Growth of E. Coli | | |
|---|---|---|---|---|
| E. coli Serotype | Biolog # | Confluent Colonies | Crowded Colonies | Single Colonies |
| Unknown (verotoxin-negative) | 287 | Red | Red | Red |
| 026:H11 | 13664 | Purple | Purple | Red |
| 026:H11 | 13665 | Blue/Purple | Blue/Purple | Blue/Purple |
| 0111:H8 | 13662 | Red/Purple | Red/Purple | Red |
| 0111:H8 | 13663 | Purple | Purple | Red |
| 0151:H7 | 11547 | Black | Black | Black |

As the above table shows, excellent results were observed with this medium. Non-pathogenic and non-verotoxin-producing E. coli (i.e., 287) grew as red colonies, while E. coli 0157:H7 grew as black colonies, and other verotoxin-producing E. coli serotypes grew as purple or blue colonies (e.g., 026:H11 and 0111:H8), except in some instances where the colonies were well-isolated.

The black coloration of the E. coli 0157:H7 strain in these Examples appeared to be unique and highly characteristic. Also, very surprising and completely unanticipated was the observation that some other isolates of verotoxin-producing E. coli serotypes may be differentiated on this medium from non-pathogenic or non-verotoxin-producing E. coli serotypes. Except for E. coli 0157:H7, all of the other E. coli serotypes were positive for utilization of sorbitol, lactose and glucuronides. However, the verotoxin-producing E. coli isolates were capable of at least partial utilization of the chromogenic galactosidase substrate in this medium, so that they form colonies that are colored purple to blue. Thus, the medium of the present invention is highly valuable, as it facilitates the isolation and identification of other verotoxin-producing E. coli isolates in addition to 0157:H7.

In conclusion, this medium formulation results in optimum differentiation between E. coli 0157:H7, other verotoxin-producing E. coli serotypes, and non-pathogenic E. coli, while selecting against Gram-positives and P. aeruginosa.

EXAMPLE 12

Use of Itaconic Acid, Propionic Acid and Other Carbon Sources to Detect Salmonella Species In this example, the observations about the selective utility of propionic acid for E. coli and Salmonella spp., from the previous examples were extended. Mixtures of selective carbon sources were tested for their effect on the growth and colony coloration of various Salmonella species, along with K. oxytoca, and E. coli, as closely-related negative controls.

A basal medium was prepared which contained agar (15 g/l), Difco proteose peptone #3 (2.5 g/l), $Na_2HPO_4$ (7 g/l), $KH_2PO_4$ (3 g/l), $MgSO_4$ (100 m (100 ml/l of a 1% solution prepared in water) and tetrazolium violet (50 mg/l). This basal medium was divided into eighteen batches, with each batch containing at least one additional ingredient. Batch #1 contained 2 g/l sodium citraconic acid; batch #2 contained 2 g/l sodium mesaconic acid; batch #3 contained 2 g/l of sodium itaconic acid, added as a 10% solution prepared in sterile water; batch #4, and all subsequent batches contained both 2 g/l sodium itaconic acid and 1 g/l sodium propionate; in addition, batch #5 contained 1 g/l propionylcholine; batch #6 contained 1 g/l D-glucosaminic acid; batch #7 contained 1 g/l ammonium citrate (($NH_4)_2$ citrate); batch #8 contained 1 g/l tricarballylic acid; batch #9 contained 1 g/l para-hydroxy-phenylacetate; batch #10 contained 1 g/l sodium α-ketobutyrate; batch #11 contained 1 g/l L-threonine; batch #12 contained 1 g/l D-threonine; batch #13 contained 1 g/l D-aspartic acid; batch #14 contained 1 g/l tyramine HCl; batch #15 contained 1 g/l 2-aminoethanol HCl; batch #16 contained 1 g/l 1,2 propanediol; batch #17 contained 1 g/l N-acetyl mannosamine; and batch #18 contained 1 g/l α-methyl mannoside. The media were microwaved and dispensed as described in Example 1.

Plates from each batch were streaked with various organisms listed in Table 6, including E. coli (ATCC 11775), E. coli 0157:H7, S. enteritidis, S. choleraesuis, S. paratyphi A, S. paratyphi C, S. typhi, SS2, SS3, SS4, SS5, SS6, and K. oxytoca. After incubation overnight (18–24 hours) at 35° C., the plates were observed for growth and colony characteristics. The following table shows the growth and colorization of these organisms on the various batches. The "+" indicates good purple colorization of the colonies; "++" indicates that the colonies were very strongly colored; "+/−" indicates that the colonies were weakly colored; "−/+" indicates that the colonies were very weakly colored; "−" indicates no colorization or no growth of the organism; and "(+)" indicates that the colonies became colored after prolonged incubation (i.e., a delayed positive result).

The best coloration and growth was obtained with batches #6 (with D-glucosaminic acid), #7 (with citric acid), #8 (with tricarballylic acid), #9 (with p-hydroxy-phenylacetate), #13 (with D-aspartic acid), #14 (with tyramine), and #17 (with N-acetyl mannosamine). In particular, batches #8 and #13 were considered to be the best, as they produced at least a weak positive reaction for all Salmonella strains tested, including the problematic S. typhi and S. paratyphi A, with little or no positive reactivity for the closely related strains of Escherichia and Klebsiella.

Based on these results, it was determined that inclusion of itaconic acid, propionic acid, tricarballylic acid and D-aspartic acid produced a good combination for detection of Salmonella species.

hanol produced very slightly better growth of S. typhi, and S. paratyphi A. On batch #5, α-ketobutyrate inhibited S.

TABLE 10

Colonial Characteristics of Organisms

| Batch: | E.c. | S.e. | S.c. | S.p. | S.t. | SS2 | SS3 | SS4 | SS5 | SS6 | K.o. |
|---|---|---|---|---|---|---|---|---|---|---|---|
| 1  | –   | –  | –   | –   | –   | –   | –   | –   | –   | –   | –   |
| 2  | –   | –  | –   | –   | –   | –   | –/+ | –   | –   | –   | –   |
| 3  | –   | –  | +/– | –   | –   | –   | –   | –   | –   | –   | –   |
| 4  | –   | +  | +   | +   | –/+ | +/– | –   | +   | –/+ | –/+ | –   |
| 5  | +   | +  | +   | +   | +/– | +/– | –   | +   | –/+ | –/+ | –   |
| 6  | –   | ++ | –/+ | ++  | –/+ | ++  | –   | ++  | +/– | ++  | –   |
| 7  | –   | ++ | ++  | ++  | –/+ | +   | –/+ | +   | +   | +   | –/+ |
| 8  | –   | +  | +   | +   | +/– | +   | +   | +   | +   | +   | –/+ |
| 9  | –   | +  | +   | +/– | –/+ | ++  | +/– | ++  | –/+ | ++  | +   |
| 10 | +/– | +  | +/– | –/+ | +/– | +   | –   | +/– | –/+ | +/– | +*  |
| 11 | –   | +  | +   | +   | –/+ | +/– | –   | +   | +/– | +   | –   |
| 12 | –   | +  | +   | +   | –/+ | +/– | –   | +   | –/+ | –/+ | –   |
| 13 | –   | ++ | +/– | +   | +   | +   | +/– | +   | +   | +   | –   |
| 14 | –   | ++ | ++  | +/– | –   | ++  | –   | ++  | –/+ | –/+ | +   |
| 15 | –   | ++ | +   | +   | –/+ | +/– | –   | +   | –/+ | –/+ | –   |
| 16 | –   | +  | +   | +   | –/+ | +/– | –   | +   | –/+ | –/+ | –   |
| 17 | –/+ | ++ | ++  | ++  | +/– | +   | –/+ | +   | +/– | +   | +/– |
| 18 | –   | +  | +   | +   | –/+ | +/– | –   | +   | –/+ | –/+ | –   |

* = Yellow colonies.

EXAMPLE 13

Use of Propionic, Tricarballylic, D-Aspartic, and Itaconic Acids and Other Carbon Sources to Detect Salmonella Species In this example, various concentrations of propionic, tricarballylic, D-aspartic, itaconic and other acids were tested for their effects on the growth and coloration of Salmonella in the presence of a tetrazolium dye. A basal medium was prepared which contained agar (15 g/l), Difco proteose peptone #3 (2.5 g/l), , Na$_2$HPO$_4$ (7 g/l), KH$_2$PO$_4$ (3 g/l), MgSO$_4$ (0.1 g/l), tetrazolium violet (50 mg/l), sodium propionate (1 g/l), sodium tricarballylic acid (10 ml/l of a 10% solution prepared in sterile water), and sodium D-aspartic acid (10 ml/l of a 10% solution prepared in sterile water). This basal medium was divided into eighteen batches, with each batch containing at least one additional ingredient. Batch #1 contained no additional components. Batches #2 and #11 contained 1 g/l propionylcholine; batches #3 and #12 contained 1 g/l ethanolamine-HCl; batches #4 and #13 contained 20 ml/l of a 10% solution of sodium mesaconic acid; batches #5 and #14 contained 0.5 g/l α-ketobutyrate; batches #6 and #15 contained 0.5 g/l tyramine-HCl; batches #7 and #16 contained 0.5 g/l para-hydroxyphenylacetate; batches #8 and #17 contained 1 g/l D-glucosaminic acid; batches #9 and #18 contained 0.5 g/l methyl-glucuronide; batches #10 through #18 also contained sodium itaconic acid (20 ml/l of a 10% solution prepared in sterile water) and catalase (100 ml/l of a 1% solution prepared in sterile water). The media were microwaved and dispensed as described in Example 1.

Plates from each batch were streaked with the same organisms as used in Example 12. After incubation overnight (18–24 hours) at 35° C., the plates were observed for growth and colony characteristics.

By comparing batch #1 with batches #4 and #10, the surprising result was observed that propionic acid utilization of E. coli was inhibited by both itaconic acid and mesaconic acid. On batches #2 and #3, propionylcholine and aminoet-typhi. On batch #6, tyramine helped SS3, but inhibited the coloration of S. typhi. On batch #7, para-hydroxyphenylacetate very slightly inhibited the coloration of S. paratyphi A. On batch #8, D-glucosaminic acid helped S. paratyphi A and S. typhi. On batch #9, methyl-glucuronide had no effect on the growth or coloration of the organisms. Batches #10–18 were very similar to or slightly better than, their respective batches #1–9. D-glucosaminic acid was the most beneficial addition, and batch #17 was the best overall.

EXAMPLE 14

Use of Propionic, Itaconic, Tricarballylic, D-Aspartic Acid, D-Glucosaminic Acids and other Carbon Sources to Detect Salmonella Species In this example, the effect of various carbon sources of varying concentrations on the reactions of the various organisms was tested, based on the observations made in the previous example. A basal medium was prepared which contained agar (15 g/l), Difco proteose peptone #3 (2.5 g/l), Na$_2$HPO$_4$ (7 g/l), KH$_2$PO$_4$ (3 g/l), MgSO$_4$ (100 mg/l), tetrazolium violet (50 mg/l), sodium propionate (1 g/l), D-glucosaminic acid (1 g/l), sodium itaconic acid (20 ml/l of a 10% solution prepared in sterile water), sodium tricarballylic acid (10 ml/l of a 10% solution prepared in sterile water), and sodium D-aspartic acid (10 ml/l of a 10% solution prepared in sterile water). This basal medium was divided into nine batches, with batches #2–9 containing at least one additional ingredient or supplemental quantities of the ingredients in the basal medium. Batch #1 contained no additional or supplemental ingredients. Batch #2 contained 0.5 g/l sodium propionate; batch #3 contained 1 g/l sodium propionate; batch #4 contained 0.5 g/l tricarballylic acid; batch #5 contained 1 g/l tricarballylic acid; batch #6 contained 1 g/l L-threonine; batch #7 contained 1 g/l propionylcholine; batch #8 contained 1 g/l ethanolamine-HCl; and batch #9 contained 0.5 g/l ammonium citrate ((NH$_4$)$_2$ citrate). The media were microwaved and dispensed as described in Example 1.

Plates from each batch were streaked for isolation with *E. coli* (ATCC #11775), *S. enteritidis, S. choleraesuis, S. paratyphi* A, *S. paratyphi* C, *S. typhi,* SS2–SS6, and *K. oxytoca.* After incubation overnight (18–24 hours) at 35°, the plates were observed for growth and colony characteristics.

On batch #1 (i.e., the basal medium), there was no purple coloration of *E. coli* nor *S. choleraesuis,* and *K. oxytoca* had a very slight purple coloration. *S. enteritidis* and SS2 both grew very well with strong coloration, and SS4, SS5, and SS6 grew almost as well. The growth and coloration of the *S. paratyphi* A and C, *S. typhi,* and SS3 was also reasonably good. In comparison with the other batches, there appeared to be no effect due to the presence of an added 0.5 g/l sodium propionate (batch #2) or propionylcholine (batch #7). Batch #3 (with an added 1 g/l sodium propionate) produced results very slightly worse than batch #1. Batch #4 was very slightly better for SS3. On batches #5 and #6, all of the organisms were slightly darker, including *K. oxytoca,* which was undesirable. On batch #8, *S. paratyphi* A and C were very slightly inhibited. However, of all these formulae, batch #9 produced the best results, with good coloration and growth of all the Salmonella species (including *S. choleraesuis,* which was uncolored on batch #1). *K. oxytoca* was also slightly positive on batch #9.

Upon review of the results of Examples #12–14, it is clear that selective growth and coloration of all Salmonella serogroups and species may be obtained by using a combination of carbon sources such as propionic acid, itaconic acid, tricarballylic acid, D-aspartic acid, D-glucosaminic acid, and citric acid. Due to the inclusion of propionic acid in this mixture, the medium also has selective properties against many other species.

EXAMPLE 15

Use of Various Other Carbon Sources

In this example, the effect of various carbon sources of varying concentrations on the reactions of the various organisms is tested, based on the observations made in the previous example. A basal medium is prepared which contained agar (15 g/l), Difco proteose peptone #3 (2.5 g/l), $Na_2HPO_4$ (7 g/l), $KH_2PO_4$ (3 g/l), $MgSO_4$ (100 mg/l), tetrazolium violet (50 mg/l), sodium propionate (1 g/l). In addition, approximately 1 g/l of methylglucuronide, lactose, D-malic acid, L-galactonic acid lactone, and D-galacturonic acid, are added. The media are microwaved and dispensed as described in Example 1.

Plates from each batch are streaked with a sample suspected of containing *E. coli,* incubated overnight (18–24 hours) at 35°, and observed for growth and colony characteristics.

It is clear that the present invention provides a highly useful medium for the rapid and reliable isolation and differentiation of organisms important in the water, food and dairy industries. This is of particular importance in view of the requirements for microbial testing mandated by the federal and state governments. By providing media which permit such rapid and reliable isolation and differentiation of such pathogens as *E. coli* 0157:H7 and Salmnonella, the present invention represents a significant contribution to the public health and welfare.

What is claimed is:

1. A method for detecting the presence of enteric bacteria selected from the group consisting of *Escherichia coli,* Salmonella, and a mixture of *Escherichia coli* and Salmonella, in a test sample suspected of containing said enteric bacteria and other bacteria, comprising the steps of:
   a) inoculating a nutrient culture medium with said test sample suspected of containing said enteric bacteria to produce an inoculated medium, wherein said nutrient culture medium comprises:
      i) a concentration of a compound selected from the group consisting of propionic acid, propionate salts, and a mixture of propionic acid and propionate salts, wherein said concentration is effective to inhibit growth of said other bacteria and to allow growth of said enteric bacteria; and
      ii) one or more chromogenic compounds, wherein said one or more chromogenic compounds results in one or more colored products in the presence of said enteric bacteria;
   b) incubating said inoculated medium under conditions wherein said enteric bacteria can grow; and
   c) detecting colored colonies on said inoculated medium, wherein the color of said colored colonies distinguishes said enteric bacteria from said other bacteria in the presence of said chromogenic compounds, thereby detecting the presence of said enteric bacteria.

2. The method of claim 1, wherein said chromogenic compound is inhibitable.

3. The method of claim 1, wherein said chromogenic compound is selected from the group consisting of galactosidase substrates and glucuronidase substrates.

4. The method of claim 3, wherein said medium further comprises one or more compounds selected from the group consisting of sorbitol, arabitol, and cellobiose.

5. The method of claim 3, wherein said chromogenic glucuronidase substrate is selected from the group consisting of 6-chloro-3-indolyl-β-D-glucuronide, 5-bromo-6-chloro-3-indolyl-β-D-glucuronide, and 5-bromo-4-chloro-3-indoxyl-β-glucuronide.

6. The method of claim 3 wherein said chromogenic galactosidase compound is selected from the group consisting of indoxyl-β-D-galactoside, 5-bromo-3-indolyl-β-D-galactoside, and 5-bromo-4-chloro-3-indolyl-β-D-galactoside.

7. The method of claim 1, wherein said medium is a broth.

8. The method of claim 1, wherein said medium further comprises a gelling agent.

9. The method of claim 1, wherein said medium further comprises one or more carbon sources selected from the group consisting of methyl-glucuronide, lactose, D-malic acid, L-galactonic acid lactone, D-galacturonic acid, itaconic acid, tricarballylic acid, α-keto-butyric acid, D-aspartic acid, glucosaminic acid, citric acid, threonine, para-hydroxyphenylacetic acid, ethanolamine, N-acetylmannosamine, and tyramine.

10. The method of claim 1, wherein said propionate salt is sodium propionate, and said concentration of said sodium propionate is from 1 g/l to 3 g/l.

11. The method of claim 10, wherein said concentration of said sodium propionate is 2.5 g/l.

12. A method for detecting the presence of enteric bacteria selected from the group consisting of *Escherichia coli,* Salmonella, and a mixture of *Escherichia coli* and Salmonella in a test sample suspected of containing said enteric bacteria and other bacteria, comprising the steps of:
   a) inoculating an enrichment medium with said test sample suspected of containing said enteric bacteria;
   b) incubating said enrichment medium under conditions wherein said enteric bacteria grow to produce an enriched sample;

c) inoculating a nutrient culture medium with said enriched sample to produce an inoculated medium, wherein said nutrient culture medium comprises:
  i) a concentration of a compound selected from the group consisting of propionic acid, propionate salts, and a mixture of propionic acid and propionate salts, wherein said concentration is effective to inhibit growth of said other bacteria and to allow growth of said enteric bacteria; and
  ii) one or more chromogenic compounds, wherein said one or more chromogenic compounds results in one or more colored products in the presence of said enteric bacteria;
d) incubating said inoculated medium under conditions wherein said enteric bacteria can grow; and
e) detecting colored colonies on said inoculated medium, wherein the color of said colored colonies distinguishes said enteric bacteria from said other bacteria in the presence of said chromogenic compounds, thereby detecting the presence of said enteric bacteria.

13. The method of claim 12, wherein said enrichment medium comprises a concentration of a compound selected from the group consisting of propionic acid, prolpionate salts, and a mixture of propionic acid and propionate salts, wherein said concentration is effective to inhibit growth of said other bacteria and to allow growth of said enteric bacteria.

14. The method of claim 13, wherein said propionate salt in said enrichment medium is sodium propionatc, and said concentration of said sodium propionate is from 1 g/l to 3 g/l.

15. The method of claim 14, wherein said concentration of said sodium propionate is 2.5 g/l.

16. The method of claim 12, wherein said chromogenic compound is inhibitable.

17. The method of claim 12, wherein said enrichment medium further comprises one or more carbon sources selected from the group consisting of methyl-glucuronide, $\alpha$-D-lactose, D-malic acid, L-galactonic acid lactone, D-galacturonic acid, itaconic acid, tricarballylic acid, $\alpha$-keto-butyric acid, D-aspartic acid, D-glucosaminic acid, citric acid, L-threonine, para-hydroxyphenylacetic acid, ethanolamine, N-acetylmannosamine, and tyramine.

18. The method of claim 12, wherein said test medium further comprises one or more carbon sources selected from the group consisting of methyl-glucuronide, $\alpha$-D-lactose, D-malic acid, L-galactonic acid lactone, D-galacturonic acid, itaconic acid, tricarballylic acid, $\alpha$-keto-butyric acid, D-aspartic acid, D-glucosaminic acid, citric acid, L-threonine, para-hydroxyphenylacetic acid, ethanolamine, N-acetylmannosamine, and tyramine.

19. The method of claim 12, wherein said chromogenic compound is selected from the group consisting of galactosidase substrates and glucuronidase substrates.

20. The method of claim 19, wherein said galactosidase substrate is selected from the group consisting of indoxyl-$\beta$-D-galactoside, 5-bromo-3-indolyl-$\beta$-D-galactoside, and 5-bromo-4-chloro-3-indolyl-$\beta$-D-galactoside.

21. The method of claim 19, wherein said glucuronidase substrate is selected from the group consisting of 6-chloro-3-indolyl-$\beta$-D-glucuronide, 5-bromo-6-chloro-3-indolyl-$\beta$-D-glucuronide, and 5-bromo-4-chloro-3-indoxyl-$\beta$-glucuronide.

* * * * *